(12) United States Patent
Keller et al.

(10) Patent No.: US 11,872,231 B2
(45) Date of Patent: *Jan. 16, 2024

(54) MOIST ORAL PRODUCT COMPRISING AN ACTIVE INGREDIENT

(71) Applicant: NICOVENTURES TRADING LIMITED, London (GB)

(72) Inventors: Christopher Keller, Advance, NC (US); Ronald K. Hutchens, East Bend, NC (US); Thomas H. Poole, Winston-Salem, NC (US); Nicolas von Cosmos, Moravian Falls, NC (US); Anthony Richard Gerardi, Winston-Salem, NC (US); Chris J. Grimes, High Point, NC (US); Steven Lee Alderman, Lewisville, NC (US); Darrell Eugene Holton, Jr., Clemmons, NC (US)

(73) Assignee: Nicoventures Trading Limited, London (GB)

( * ) Notice: Subject to any disclaimer, the term of this patent is extended or adjusted under 35 U.S.C. 154(b) by 252 days.

This patent is subject to a terminal disclaimer.

(21) Appl. No.: 16/707,117

(22) Filed: Dec. 9, 2019

(65) Prior Publication Data

US 2021/0169889 A1 Jun. 10, 2021

(51) Int. Cl.
| | |
|---|---|
| A61K 31/522 | (2006.01) |
| A61K 31/197 | (2006.01) |
| A61K 9/00 | (2006.01) |
| A61K 36/258 | (2006.01) |
| A61K 47/18 | (2017.01) |
| A24B 15/16 | (2020.01) |
| A61K 31/675 | (2006.01) |
| A61K 31/714 | (2006.01) |
| A61K 47/38 | (2006.01) |
| A24B 13/00 | (2006.01) |
| A61K 31/465 | (2006.01) |

(52) U.S. Cl.
CPC ............ *A61K 31/522* (2013.01); *A24B 13/00* (2013.01); *A24B 15/16* (2013.01); *A61K 9/009* (2013.01); *A61K 31/197* (2013.01); *A61K 31/465* (2013.01); *A61K 31/675* (2013.01); *A61K 31/714* (2013.01); *A61K 36/258* (2013.01); *A61K 47/18* (2013.01); *A61K 47/38* (2013.01)

(58) Field of Classification Search
None
See application file for complete search history.

(56) References Cited

U.S. PATENT DOCUMENTS

| | | |
|---|---|---|
| 3,339,558 A | 9/1967 | Waterbury |
| 3,390,686 A | 7/1968 | Irby et al. |
| 3,550,598 A | 12/1970 | McGlumphy et al. |
| 3,685,521 A | 8/1972 | Dock |
| 3,916,914 A | 11/1975 | Brooks et al. |
| 4,241,093 A | 12/1980 | Farag et al. |
| 4,737,323 A | 4/1988 | Martin et al. |
| 4,889,144 A | 12/1989 | Tateno et al. |
| 4,997,654 A | 3/1991 | Corsello et al. |
| 5,004,595 A | 4/1991 | Cherukuri et al. |
| 5,223,185 A | 6/1993 | Takei et al. |
| 5,292,528 A | 3/1994 | Mori et al. |
| 5,387,093 A | 2/1995 | Takei et al. |
| 5,387,416 A | 2/1995 | White et al. |
| 5,417,229 A | 5/1995 | Summers et al. |
| 5,472,002 A | 12/1995 | Covarrubias |
| 5,525,351 A | 6/1996 | Dam |
| 5,690,990 A | 11/1997 | Bonner |
| 5,759,599 A | 6/1998 | Wampler et al. |
| 5,811,126 A | 9/1998 | Krishnamurthy |
| 5,882,680 A | 3/1999 | Suzuki et al. |
| 6,039,901 A | 3/2000 | Soper et al. |
| 6,045,835 A | 4/2000 | Soper et al. |
| 6,056,992 A | 5/2000 | Lew |
| 6,060,078 A | 5/2000 | Lee |
| 6,106,875 A | 8/2000 | Soper et al. |
| 6,117,455 A | 9/2000 | Takada et al. |
| 6,138,683 A | 10/2000 | Hersh et al. |
| 6,261,589 B1 | 7/2001 | Pearson et al. |
| 6,325,859 B1 | 12/2001 | DeRoos et al. |
| 6,482,433 B1 | 11/2002 | DeRoos et al. |
| 6,596,298 B2 | 7/2003 | Leung et al. |
| 6,612,429 B2 | 9/2003 | Dennen |
| 6,631,722 B2 | 10/2003 | MacAdam et al. |
| 6,719,933 B2 | 4/2004 | Nakamura et al. |
| 6,845,777 B2 | 1/2005 | Pera |
| 6,929,814 B2 | 8/2005 | Bouwmeesters et al. |

(Continued)

FOREIGN PATENT DOCUMENTS

| | | |
|---|---|---|
| AU | 2004/275843 | 4/2008 |
| CA | 3042133 A1 | 5/2018 |

(Continued)

OTHER PUBLICATIONS

Dvoryanchikov, Gennady et al., "GABA, its receptors, and GABAergic inhibition in mouse taste buds" J. Neurosci. Apr. 13, 2011;31(15):5782-91.

(Continued)

*Primary Examiner* — Melissa S Mercier
(74) *Attorney, Agent, or Firm* — Womble Bond Dickinson (US) LLP

(57) ABSTRACT

The disclosure provides a composition configured for oral use, the composition including a filler in an amount of at least 20% by weight, based on the total weight of the composition, and at least one active ingredient including one or more botanical materials, stimulants, amino acids, vitamins, antioxidants, cannabinoids, pharmaceutical agents, or a combination thereof. The composition further includes a salt and at least one sweetener. The composition has a moisture content of at least about 40% by weight, based on the total weight of the composition.

24 Claims, 1 Drawing Sheet

(56) References Cited

U.S. PATENT DOCUMENTS

| | | |
|---|---|---|
| 6,949,256 B2 | 9/2005 | Fonkwe et al. |
| 6,958,143 B2 | 10/2005 | Choi et al. |
| 7,032,601 B2 | 4/2006 | Atchley et al. |
| 7,056,541 B1 | 6/2006 | Stahl et al. |
| 7,067,150 B2 | 6/2006 | Farber et al. |
| 7,115,085 B2 | 10/2006 | Deal |
| 7,494,669 B2 | 2/2009 | Ni et al. |
| 7,507,427 B2 | 3/2009 | Andersen et al. |
| 7,531,192 B2 | 5/2009 | Farber et al. |
| 7,810,507 B2 | 10/2010 | Dube et al. |
| 7,833,555 B2 | 11/2010 | Andersen et al. |
| 7,861,728 B2 | 1/2011 | Holton, Jr. et al. |
| 7,900,637 B2 | 3/2011 | Fagerstrom et al. |
| 7,946,295 B2 | 5/2011 | Brinkley et al. |
| 7,950,399 B2 | 5/2011 | Winterson et al. |
| 8,069,861 B2 | 12/2011 | Sinclair |
| 8,124,147 B2 | 2/2012 | Cheng et al. |
| 8,293,295 B2 | 10/2012 | Andersen et al. |
| 8,336,557 B2 | 12/2012 | Kumar et al. |
| 8,343,532 B2 | 1/2013 | Dam et al. |
| 8,424,541 B2 | 4/2013 | Crawford et al. |
| 8,469,036 B2 | 6/2013 | Williams et al. |
| 8,469,037 B2 | 6/2013 | Liu et al. |
| 8,529,875 B2 | 9/2013 | Andersen |
| 8,529,914 B2 | 9/2013 | Fuisz et al. |
| 8,545,870 B2 | 10/2013 | Dupinay et al. |
| 8,591,967 B2 | 11/2013 | Andersen et al. |
| 8,613,285 B2 | 12/2013 | Fuisz |
| 8,627,828 B2 | 1/2014 | Strickland et al. |
| 8,642,016 B2 | 2/2014 | Chau et al. |
| 8,714,163 B2 | 5/2014 | Kumar et al. |
| 8,741,348 B2 | 6/2014 | Hansson et al. |
| 8,747,562 B2 | 6/2014 | Mishra et al. |
| 8,828,361 B2 | 9/2014 | Anderson |
| 8,833,378 B2 | 9/2014 | Axelsson et al. |
| 8,846,075 B2 | 9/2014 | Johnson et al. |
| 8,858,984 B2 | 10/2014 | Dam et al. |
| 8,863,755 B2 | 10/2014 | Zhuang et al. |
| 8,871,243 B2 | 10/2014 | Fankhauser et al. |
| 8,931,493 B2 | 1/2015 | Sebastian et al. |
| 8,945,593 B2 | 2/2015 | LoCoco et al. |
| 8,978,661 B2 | 3/2015 | Atchley et al. |
| 8,992,974 B2 | 3/2015 | McCarty |
| 9,027,567 B2 | 5/2015 | Gee et al. |
| 9,039,839 B2 | 5/2015 | Beeson et al. |
| 9,044,035 B2 | 6/2015 | Jackson et al. |
| 9,084,439 B2 | 7/2015 | Holton, Jr. |
| 9,155,321 B2 | 10/2015 | Cantrell et al. |
| 9,155,772 B2 | 10/2015 | Gao et al. |
| 9,161,567 B2 | 10/2015 | Shikata et al. |
| 9,161,908 B2 | 10/2015 | Nilsson |
| 9,167,835 B2 | 10/2015 | Sengupta et al. |
| 9,185,931 B2 | 11/2015 | Gao et al. |
| 9,204,667 B2 | 12/2015 | Cantrell et al. |
| 9,237,768 B2 | 1/2016 | Carroll et al. |
| 9,358,296 B2 | 6/2016 | McCarty |
| 9,372,033 B2 | 6/2016 | Lampe et al. |
| 9,375,033 B2 | 6/2016 | Lampe et al. |
| 9,386,800 B2 | 7/2016 | Sebastian et al. |
| 9,402,414 B2 | 8/2016 | Griscik et al. |
| 9,402,809 B2 | 8/2016 | Axelsson et al. |
| 9,402,810 B2 | 8/2016 | Nilsson |
| 9,414,624 B2 | 8/2016 | Carroll et al. |
| 9,420,825 B2 | 8/2016 | Beeson et al. |
| 9,468,233 B2 | 10/2016 | Macko et al. |
| 9,474,303 B2 | 10/2016 | Holton, Jr. |
| 9,521,864 B2 | 12/2016 | Gao et al. |
| 9,565,867 B2 | 2/2017 | Wittorff et al. |
| 9,629,392 B2 | 4/2017 | Holton, Jr. |
| 9,675,102 B2 | 6/2017 | Hunt et al. |
| 9,763,928 B2 | 9/2017 | Duggins et al. |
| 9,775,376 B2 | 10/2017 | Cantrell et al. |
| 9,801,409 B1 | 10/2017 | Smith |
| 9,848,634 B2 | 12/2017 | Fuisz |
| 9,854,830 B2 | 1/2018 | Gao et al. |
| 9,884,015 B2 | 2/2018 | Gao et al. |
| 9,907,748 B2 | 3/2018 | Borschke et al. |
| 9,925,145 B2 | 3/2018 | Hubinette et al. |
| 9,930,909 B2 | 4/2018 | Gao et al. |
| 9,950,858 B2 | 4/2018 | Byrd et al. |
| 9,999,243 B2 | 6/2018 | Gao et al. |
| 10,039,309 B2 | 8/2018 | Carroll et al. |
| 10,045,976 B2 | 8/2018 | Fusco et al. |
| 10,092,715 B2 | 10/2018 | Axelsson et al. |
| 10,130,120 B2 | 11/2018 | Mishra et al. |
| 10,143,230 B2 | 12/2018 | Mishra et al. |
| 10,149,850 B2 | 12/2018 | Mishra et al. |
| 10,172,810 B2 | 1/2019 | McCarty |
| 10,244,786 B2 | 4/2019 | Gao et al. |
| 10,328,023 B2 | 6/2019 | Romanoschi et al. |
| 10,334,873 B2 | 7/2019 | Mishra et al. |
| 10,349,672 B2 | 7/2019 | Gao et al. |
| 10,357,054 B2 | 7/2019 | Marshall et al. |
| 10,369,182 B2 | 8/2019 | Cohen |
| 10,375,984 B2 | 8/2019 | Hernandez Garcia et al. |
| 10,390,557 B2 | 8/2019 | Börjesson et al. |
| 10,426,726 B2 | 10/2019 | Neergaard |
| 10,463,070 B2 | 11/2019 | Carroll et al. |
| 10,517,322 B1 | 12/2019 | Lee |
| 10,532,046 B2 | 1/2020 | Rogers et al. |
| 10,543,205 B2 | 1/2020 | Wittorff et al. |
| 10,881,132 B2 | 1/2021 | Mua et al. |
| 2001/0045215 A1 | 11/2001 | Meyer et al. |
| 2002/0006919 A1 | 1/2002 | Thosar et al. |
| 2003/0003130 A1 | 1/2003 | Okubo et al. |
| 2003/0224090 A1 | 4/2003 | Pearce et al. |
| 2003/0118628 A1 | 6/2003 | Tutuncu et al. |
| 2004/0118422 A1 | 6/2004 | Lundin et al. |
| 2004/0123873 A1 | 7/2004 | Calandro et al. |
| 2004/0191322 A1 | 9/2004 | Hansson |
| 2004/0224020 A1 | 11/2004 | Schoenhard |
| 2004/0261807 A1 | 12/2004 | Dube et al. |
| 2005/0061339 A1 | 3/2005 | Hansson et al. |
| 2005/0123601 A1 | 6/2005 | Mane et al. |
| 2005/0196437 A1 | 9/2005 | Bednarz et al. |
| 2005/0244521 A1 | 11/2005 | Strickland et al. |
| 2005/0249676 A1 | 11/2005 | Scott et al. |
| 2006/0130861 A1 | 6/2006 | Luan et al. |
| 2006/0144412 A1 | 7/2006 | Mishra et al. |
| 2006/0174901 A1 | 8/2006 | Karles et al. |
| 2006/0191548 A1 | 8/2006 | Strickland et al. |
| 2006/0263414 A1 | 11/2006 | Pan et al. |
| 2006/0272663 A1 | 12/2006 | Dube et al. |
| 2007/0012327 A1 | 1/2007 | Karles et al. |
| 2007/0031539 A1 | 2/2007 | Calton |
| 2007/0062549 A1 | 3/2007 | Holton, Jr. et al. |
| 2007/0082101 A1 | 4/2007 | Wiesmuller |
| 2007/0092554 A1 | 4/2007 | Lindberg et al. |
| 2007/0095357 A1 | 5/2007 | Besso et al. |
| 2007/0148292 A1 | 6/2007 | Royo et al. |
| 2007/0184093 A1 | 8/2007 | Hang |
| 2007/0186941 A1 | 8/2007 | Holton et al. |
| 2007/0261707 A1 | 11/2007 | Winterson et al. |
| 2007/0269386 A1 | 11/2007 | Steen et al. |
| 2008/0029110 A1 | 2/2008 | Dube et al. |
| 2008/0029117 A1 | 2/2008 | Mua et al. |
| 2008/0081071 A1 | 4/2008 | Sanghvi et al. |
| 2008/0142025 A1 | 6/2008 | Sinclair |
| 2008/0166395 A1 | 7/2008 | Roush |
| 2008/0202536 A1 | 8/2008 | Torrence et al. |
| 2008/0233245 A1 | 9/2008 | White et al. |
| 2008/0308115 A1 | 12/2008 | Zimmermann |
| 2008/0317911 A1 | 12/2008 | Schleef et al. |
| 2009/0023819 A1 | 1/2009 | Axelsson |
| 2009/0025739 A1 | 1/2009 | Brinkley et al. |
| 2009/0053388 A1 | 2/2009 | Powers et al. |
| 2009/0065013 A1 | 3/2009 | Essen et al. |
| 2009/0087514 A1 | 4/2009 | Breeden |
| 2009/0095313 A1 | 4/2009 | Fuisz |
| 2009/0142443 A1 | 6/2009 | Robinson et al. |
| 2009/0253754 A1 | 10/2009 | Selmin et al. |
| 2009/0263476 A1 | 10/2009 | Jobdevairakkam et al. |
| 2009/0301504 A1 | 12/2009 | Worthen et al. |
| 2010/0004294 A1 | 1/2010 | Axelsson et al. |

(56) References Cited

U.S. PATENT DOCUMENTS

| | | |
|---|---|---|
| 2010/0018541 A1 | 1/2010 | Gerardi et al. |
| 2010/0061940 A1 | 3/2010 | Axelsson et al. |
| 2010/0126520 A1* | 5/2010 | Clayton .............. A24B 15/30 |
| | | 131/277 |
| 2010/0187143 A1 | 7/2010 | Essen et al. |
| 2010/0218779 A1 | 9/2010 | Zhuang et al. |
| 2010/0260690 A1 | 10/2010 | Kristensen et al. |
| 2010/0291245 A1 | 11/2010 | Gao et al. |
| 2010/0294292 A1 | 11/2010 | Hodin et al. |
| 2010/0300464 A1 | 12/2010 | Gee et al. |
| 2010/0326454 A1 | 12/2010 | Fuisz |
| 2011/0083680 A1 | 4/2011 | Mishra et al. |
| 2011/0083681 A1 | 4/2011 | Sengupta et al. |
| 2011/0104218 A1 | 4/2011 | Mishra et al. |
| 2011/0129517 A1 | 6/2011 | Rudolph et al. |
| 2011/0139164 A1 | 6/2011 | Mua et al. |
| 2011/0139166 A1 | 6/2011 | Luzenberg, Jr. |
| 2011/0180087 A1 | 7/2011 | Gee et al. |
| 2011/0220130 A1 | 9/2011 | Mua et al. |
| 2011/0223297 A1 | 9/2011 | Corkery et al. |
| 2011/0232662 A1 | 9/2011 | Liu et al. |
| 2011/0236536 A1 | 9/2011 | Mongia |
| 2011/0247640 A1 | 10/2011 | Beeson et al. |
| 2011/0268809 A1 | 11/2011 | Brinkley et al. |
| 2011/0274628 A1 | 11/2011 | Borschke |
| 2011/0288132 A1 | 11/2011 | Lindberg |
| 2011/0303232 A1 | 12/2011 | Williams |
| 2012/0031415 A1 | 2/2012 | Essen et al. |
| 2012/0031416 A1 | 2/2012 | Atchley et al. |
| 2012/0037175 A1 | 2/2012 | Cantrell et al. |
| 2012/0039981 A1 | 2/2012 | Pedersen et al. |
| 2012/0103353 A1 | 5/2012 | Sebastian et al. |
| 2012/0107300 A1 | 5/2012 | Schirripa |
| 2012/0128734 A1* | 5/2012 | Hubinette ............ A61K 9/1652 |
| | | 514/343 |
| 2012/0138074 A1 | 6/2012 | Cantrell et al. |
| 2012/0138075 A1 | 6/2012 | Jespersen et al. |
| 2012/0177818 A1 | 7/2012 | Trivedi et al. |
| 2013/0005831 A1 | 1/2013 | Rajewski et al. |
| 2013/0074856 A1 | 3/2013 | Holton, Jr. |
| 2013/0078307 A1 | 3/2013 | Holton, Jr. et al. |
| 2013/0098377 A1 | 4/2013 | Borschke et al. |
| 2013/0118512 A1 | 5/2013 | Jackson et al. |
| 2013/0152953 A1 | 6/2013 | Mua et al. |
| 2013/0177646 A1 | 7/2013 | Hugerth et al. |
| 2013/0206115 A1 | 8/2013 | Kragh |
| 2013/0206150 A1 | 8/2013 | Duggins et al. |
| 2013/0206153 A1 | 8/2013 | Beeson et al. |
| 2013/0209540 A1 | 8/2013 | Duggins et al. |
| 2013/0251779 A1 | 9/2013 | Svandal et al. |
| 2013/0263870 A1 | 10/2013 | Cantrell et al. |
| 2013/0276801 A1 | 10/2013 | Byrd et al. |
| 2013/0312774 A1 | 11/2013 | Holton, Jr. |
| 2013/0330379 A1 | 12/2013 | Ylipertula et al. |
| 2013/0330417 A1 | 12/2013 | Dong et al. |
| 2013/0340773 A1 | 12/2013 | Sebastian et al. |
| 2014/0130813 A1 | 5/2014 | Strehle |
| 2014/0154301 A1 | 6/2014 | Chau et al. |
| 2014/0234392 A1 | 8/2014 | Hansson et al. |
| 2014/0255452 A1 | 9/2014 | Reddick et al. |
| 2014/0261485 A1 | 9/2014 | Kobai et al. |
| 2014/0271791 A1 | 9/2014 | Mishra et al. |
| 2014/0271946 A1 | 9/2014 | Kobai et al. |
| 2014/0332013 A1 | 11/2014 | Gao et al. |
| 2015/0068544 A1 | 3/2015 | Moldoveanu et al. |
| 2015/0068545 A1 | 3/2015 | Moldoveanu et al. |
| 2015/0071972 A1 | 3/2015 | Holton, Jr. et al. |
| 2015/0096573 A1 | 4/2015 | Gao et al. |
| 2015/0096574 A1 | 4/2015 | Gao et al. |
| 2015/0096576 A1 | 4/2015 | Gao et al. |
| 2015/0098996 A1 | 4/2015 | Gao et al. |
| 2015/0101627 A1* | 4/2015 | Marshall ............... A24B 13/00 |
| | | 131/352 |
| 2015/0230515 A1 | 8/2015 | Lampe et al. |
| 2015/0231070 A1 | 8/2015 | Huang |
| 2015/0296868 A1 | 10/2015 | Sutton |
| 2015/0368368 A1 | 12/2015 | Retsina et al. |
| 2016/0000140 A1 | 1/2016 | Sebastian et al. |
| 2016/0038552 A1 | 2/2016 | Bredesen et al. |
| 2016/0073657 A1 | 3/2016 | Campomanes et al. |
| 2016/0073676 A1 | 3/2016 | Cantrell et al. |
| 2016/0073689 A1 | 3/2016 | Sebastian et al. |
| 2016/0157515 A1 | 6/2016 | Chapman et al. |
| 2016/0165953 A1 | 6/2016 | Goode, Jr. |
| 2016/0166543 A1 | 6/2016 | Joshi et al. |
| 2016/0186377 A1 | 6/2016 | Haldane et al. |
| 2016/0192703 A1 | 7/2016 | Sebastian et al. |
| 2016/0279056 A1 | 9/2016 | Zhao et al. |
| 2016/0303042 A1 | 10/2016 | Yoshimura et al. |
| 2016/0324777 A1 | 11/2016 | Victor et al. |
| 2017/0007594 A1 | 1/2017 | Borschke |
| 2017/0028672 A1 | 2/2017 | Lim et al. |
| 2017/0099868 A1 | 4/2017 | Gao et al. |
| 2017/0157106 A1 | 6/2017 | Rogers et al. |
| 2017/0164651 A1 | 6/2017 | Mua et al. |
| 2017/0165252 A1 | 6/2017 | Mua et al. |
| 2017/0172995 A1 | 6/2017 | Repaka et al. |
| 2017/0209380 A1 | 7/2017 | Ognibene et al. |
| 2017/0210550 A1 | 7/2017 | Siu |
| 2017/0216213 A1 | 8/2017 | Ognibene et al. |
| 2017/0239336 A1 | 8/2017 | Zanetti |
| 2017/0258918 A1 | 9/2017 | Rifkin et al. |
| 2017/0258978 A1 | 9/2017 | Bartlett et al. |
| 2017/0280764 A1 | 10/2017 | Sahlen et al. |
| 2017/0312261 A1 | 11/2017 | Changoer et al. |
| 2017/0318844 A1 | 11/2017 | Gordon |
| 2017/0318858 A1 | 11/2017 | Hodin et al. |
| 2018/0044856 A1 | 2/2018 | Dhumpa et al. |
| 2018/0049979 A1 | 2/2018 | Zhao et al. |
| 2018/0051002 A1 | 2/2018 | Dull et al. |
| 2018/0140007 A1 | 5/2018 | Aspgren et al. |
| 2018/0140521 A1 | 5/2018 | Geonnotti et al. |
| 2018/0140554 A1 | 5/2018 | Wittorff |
| 2018/0153211 A1 | 6/2018 | Persson |
| 2018/0235273 A1 | 8/2018 | Carroll et al. |
| 2018/0255826 A1 | 9/2018 | Persson et al. |
| 2018/0257801 A1 | 9/2018 | Persson |
| 2018/0271112 A1 | 9/2018 | Barkalow et al. |
| 2018/0271146 A9 | 9/2018 | Aspgren et al. |
| 2018/0338892 A1 | 11/2018 | Budde et al. |
| 2019/0000907 A1 | 1/2019 | Cohen |
| 2019/0008766 A1 | 1/2019 | Favara et al. |
| 2019/0037909 A1 | 2/2019 | Greenbaum et al. |
| 2019/0060225 A1 | 2/2019 | Mandel et al. |
| 2019/0083393 A1 | 3/2019 | Axelsson et al. |
| 2019/0110514 A1 | 4/2019 | Vetter |
| 2019/0124971 A1 | 5/2019 | Soffe et al. |
| 2019/0174812 A1 | 6/2019 | Nielsen et al. |
| 2019/0175581 A1 | 6/2019 | Nielsen et al. |
| 2019/0246686 A1 | 8/2019 | Zhuang et al. |
| 2019/0254337 A1 | 8/2019 | Bjoerkholm |
| 2019/0255035 A1 | 8/2019 | Bruun |
| 2019/0313689 A1 | 10/2019 | Beeson et al. |
| 2019/0350862 A1 | 11/2019 | Wittorff |
| 2020/0037638 A1 | 2/2020 | Faraci et al. |
| 2020/0085093 A1 | 3/2020 | Gee et al. |
| 2020/0128870 A1 | 4/2020 | Hassler et al. |
| 2020/0138706 A1 | 5/2020 | Rudraraju et al. |
| 2020/0138783 A1 | 5/2020 | Rinaldi |
| 2020/0275689 A1 | 9/2020 | Lewerenz |
| 2020/0297026 A1 | 9/2020 | Kannisto et al. |
| 2020/0305496 A1 | 10/2020 | Gessesse |
| 2020/0383372 A1 | 12/2020 | Stahl et al. |
| 2020/0383373 A1 | 12/2020 | Stahl et al. |
| 2021/0023046 A1 | 1/2021 | Bruun |
| 2021/0068446 A1* | 3/2021 | Keller ................. A24B 15/183 |
| 2021/0077389 A1 | 3/2021 | Mandel et al. |
| 2022/0225659 A1 | 7/2022 | Gessesse et al. |
| 2022/0295858 A1 | 9/2022 | Holton, Jr. et al. |

FOREIGN PATENT DOCUMENTS

| | | |
|---|---|---|
| CN | 103005680 A | 4/2013 |
| CN | 103263507 A | 8/2013 |

(56) References Cited

FOREIGN PATENT DOCUMENTS

| | | |
|---|---|---|
| CN | 103494324 A | 1/2014 |
| CN | 104770860 A | 7/2015 |
| CN | 105192876 A | 12/2015 |
| CN | 105595404 A | 5/2016 |
| CN | 105916603 | 8/2016 |
| CN | 105918603 | 9/2016 |
| CN | 106805287 A | 6/2017 |
| CN | 108649170 | 10/2018 |
| CN | 104770860 | 5/2020 |
| DE | 19524197 A1 | 9/1997 |
| EP | 1951074 | 8/2008 |
| EP | 2177213 A1 | 4/2010 |
| EP | 2417967 | 2/2012 |
| EP | 2640204 | 9/2013 |
| EP | 2804498 | 11/2014 |
| EP | 2891408 | 7/2015 |
| EP | 3087852 | 11/2016 |
| GB | 2487808 A | 8/2012 |
| JP | 2004/161719 | 6/2004 |
| SE | 1750488 | 10/2018 |
| SE | 541198 C2 | 4/2019 |
| WO | WO 96/31255 | 10/1996 |
| WO | WO1997/12605 | 4/1997 |
| WO | WO2000/13662 | 3/2000 |
| WO | WO 02/080707 | 10/2002 |
| WO | WO2003/039518 | 5/2003 |
| WO | WO2003/053175 | 7/2003 |
| WO | WO2004/000273 | 12/2003 |
| WO | WO2004/056219 | 7/2004 |
| WO | WO2004/056363 | 7/2004 |
| WO | WO 2004/095959 | 11/2004 |
| WO | WO2005/046363 | 5/2005 |
| WO | WO2005041699 A2 | 5/2005 |
| WO | WO 2005/063060 | 7/2005 |
| WO | WO2006/000232 | 1/2006 |
| WO | WO2007/037962 | 4/2007 |
| WO | WO2007/053098 | 5/2007 |
| WO | WO 2007/126361 | 11/2007 |
| WO | WO2008/056135 | 5/2008 |
| WO | WO2008/101076 A1 | 8/2008 |
| WO | WO 2008/103935 | 8/2008 |
| WO | WO2008/115563 A1 | 9/2008 |
| WO | WO2009/004486 A2 | 1/2009 |
| WO | WO2009/010875 A2 | 1/2009 |
| WO | WO2009/010876 A2 | 1/2009 |
| WO | WO2009/010878 A2 | 1/2009 |
| WO | WO2009/010881 A2 | 1/2009 |
| WO | WO2009/015142 | 1/2009 |
| WO | WO2009/067734 | 6/2009 |
| WO | WO2009/108769 | 9/2009 |
| WO | WO2010/114445 A1 | 10/2010 |
| WO | WO2010/125516 | 11/2010 |
| WO | WO20100134025 A2 | 11/2010 |
| WO | WO2010/139987 | 12/2010 |
| WO | WO2011/081725 | 7/2011 |
| WO | WO2011/116977 A1 | 9/2011 |
| WO | WO2011/117740 | 9/2011 |
| WO | WO2012/143405 A1 | 10/2012 |
| WO | WO2013/119760 | 8/2013 |
| WO | WO2013/119799 | 8/2013 |
| WO | WO2014/166994 A1 | 10/2014 |
| WO | WO2015/051308 | 4/2015 |
| WO | WO2015/067372 | 5/2015 |
| WO | WO2015/067773 A1 | 5/2015 |
| WO | WO 2015/075745 | 5/2015 |
| WO | WO2015/117011 | 8/2015 |
| WO | WO 2015/160842 | 10/2015 |
| WO | WO2015/193379 | 12/2015 |
| WO | WO2016/067226 | 5/2016 |
| WO | WO2016/075371 | 5/2016 |
| WO | WO2016/090075 | 6/2016 |
| WO | WO2016/099960 A1 | 6/2016 |
| WO | WO2016/144376 | 9/2016 |
| WO | WO2016/147186 | 9/2016 |
| WO | WO2016/164470 | 10/2016 |
| WO | WO2018/009139 | 1/2018 |
| WO | WO2018/029626 | 2/2018 |
| WO | WO2018/197454 | 11/2018 |
| WO | WO-2018197454 A1 * | 11/2018 ............ A24B 13/00 |
| WO | WO2018233782 A1 | 12/2018 |
| WO | WO2019/005889 | 1/2019 |
| WO | WO2019/036243 | 2/2019 |
| WO | WO2019/094745 | 5/2019 |
| WO | WO2019/115778 | 6/2019 |
| WO | WO2019/135224 | 7/2019 |
| WO | WO2019/140406 | 7/2019 |
| WO | WO2019/219147 | 11/2019 |
| WO | WO2019219147 A1 | 11/2019 |
| WO | WO2019/232513 A1 | 12/2019 |
| WO | WO 2020/028991 | 2/2020 |
| WO | WO2020/044163 A1 | 3/2020 |
| WO | WO2020/157280 A1 | 8/2020 |
| WO | WO2021/063727 A1 | 9/2020 |
| WO | WO2020/224789 A1 | 11/2020 |
| WO | WO2020/236798 | 11/2020 |
| WO | WO2021/034403 A1 | 2/2021 |
| WO | WO2021/048792 A1 | 3/2021 |
| WO | WO2021/050741 A1 | 3/2021 |
| WO | WO2021/053036 A1 | 3/2021 |
| WO | WO2021/086367 A1 | 5/2021 |
| WO | WO-2021086367 A1 * | 5/2021 ............ A24B 13/00 |
| WO | WO2021/226542 A1 | 11/2021 |
| WO | WO2022/002996 A1 | 1/2022 |

OTHER PUBLICATIONS

Robichaud Meagan et al., "Tobacco companies introduce 'tobacco free' nicotine pouches", *Tob Control 2019*, Nov. 21, 2019, 1-2, National Library of Medicine, doi:10.1136/tobaccocontrol-2019-055321.

Ali Ashjaran et al: "Overview of bionanofabric from bacterial cellulose", The Journal of the Textile Institute, vol. 104, No. 2, Feb. 1, 2013, pp. 121-131.

Liu, Qingqing et al., "Food-Grade Nanoemulsions: Preparation, Stability and Application in Encapsulation of Bioactive Compounds" Molecules 2019, 24, 4242-4279.

Mohammaei et al: "Coefficient partition prediction of saturated monocarboxylic acids using the molecular descriptors", Journal of the Chilean Chemical Society, vol. 63, No. 3, 2018, pp. 4068-4071.

Shit, Subhas et al., "Edible Polymers: Challenges and Opportunities", Journal of Polymers vol. 2014, Article ID 427259, 13 pages; http://dx.doi.org/10.1155/2014/427259.

Umashankar et al., Chewable Lozenges Formulation a Review International Research Journal of Pharmacy, 2016, 7(4), 9-16.

Vieira, Melissa et al., "Natural-based plasticizers and biopolymer films: A review", European Polymer Journal 47, (2011), 254-263.

Acton et al., Chapter 3: Esterases from "Hydrolases—Advances in Research and Publication," 2003, p. 160.

Cash, M.J. et al., "Cellulose Derivatives," Imelson, Alan, Food Stabilisers, Thickeners and Gelling Agents, 2010, Blackwell Publishing Ltd., 1st Edition, p. 95-113.

Ester, Valerate, "Chemical Entities of Biological Interest," European Molecular Biology Laboratory, 2019, https://www.ebi.ac.uk/chebi/searchId.do?chebiId=CHEBI:50871.

Fernandes et al., "Manufacture and Characterization of Mucoadhesive Buccal Films Based on Pectin and Gellan Gum Containing Triamcinolone Acetonide," *International Journal of Polymer Science*, vol. 2018, pp. 1-10.

Friedman et al., "Cinnamaldehyde Content in Foods Determined by Gas Chromatography—Mass Spectrometry," 2000, Journal of Agricultural and Food Chemistry, vol. 48, No. 11, pp. 5702-5709.

Guntert in Takeoka, et al., "Flavor Chemistry of Peppermint Oil (*Mentha piperita* L.)," Aroma Active Compounds in Foods ACS Symposium Series; American Chemical Society: Washington, DC 2001.

Lee et al., "Gums, Jellies and Pastilles," in Sugar Confectionery and Chocolate Manufacture, 1973, pp. 226-255.

Nestor et al., "Role of Oxides of Nitrogen in Tobacco-Specific Nitrosamine Formation in Flue-Cured Tobacco" Beitrage Tabakforsch. Int., 20, 467-475 (2003).

(56) References Cited

OTHER PUBLICATIONS

Niesz, Krisztian, et al., "Sol-gel Synthesis of ordered mesoporous alumina," Chem. Commun., 2005, pp. 1986-1987.
Onal et al., "Some Physicochemical Properties Of The White Sepiolite Known As Pipestone From Kskisehir, Turkey," 2008, Clays and Clay Minerals, vol. 56, No. 5, pp. 511-519.
Perfetti, T. A. "Structural study of nicotine salts" Beitrage Tabakforschung Int., 12: 43-54 (1983).
Roton et al., "Factors Influencing the Formation of Tobacco-Specific Nitrosamines in French Air-Cured Tobaccos in Trials and at the Farm Level" Beitrage Tabakforsch. Int., 21, 305-320 (2005).
Staaf et al., "Formation of Tobacco-Specific Nitrosamines (TSNA) During Air-Curing: Conditions and Control" Beitrage Tabakforsch. Int., 21, 321-330 (2005).
Szel, et al., "Anti-irritant and anti-inflammatory effects of glycerol and xylitol in sodium lauryl sulphate-induced acute irritation," The Journal of European Academy of Dermatology and Venereology, vol. 29, Issue 12, Dec. 2015, 2333-2341.
V2 Cigs UK, "What is Synthetic Nicotine and is it safe?" Sep. 11, 2019, (https://www.buyv2cigs.co.uk/).
Kickup Purenergy Booklet; published in 2011 (see partial machine translation of p. 48).
Kickup Pouch Product Specification Sheet (Mint); product available for sale in Sweden at least as early as 2018.
Kickup Original, Softmint Salmiakki—Table of Contents—English; product available for sale in Sweden at least as early as 2018.
Kickup Strong—Table of Contents—English; product available for sale in Sweden at least as early as 2018.
Real White Original & Soft Mint—Table of Contents-English; product available for sale in Sweden at least as early as 2018.

\* cited by examiner

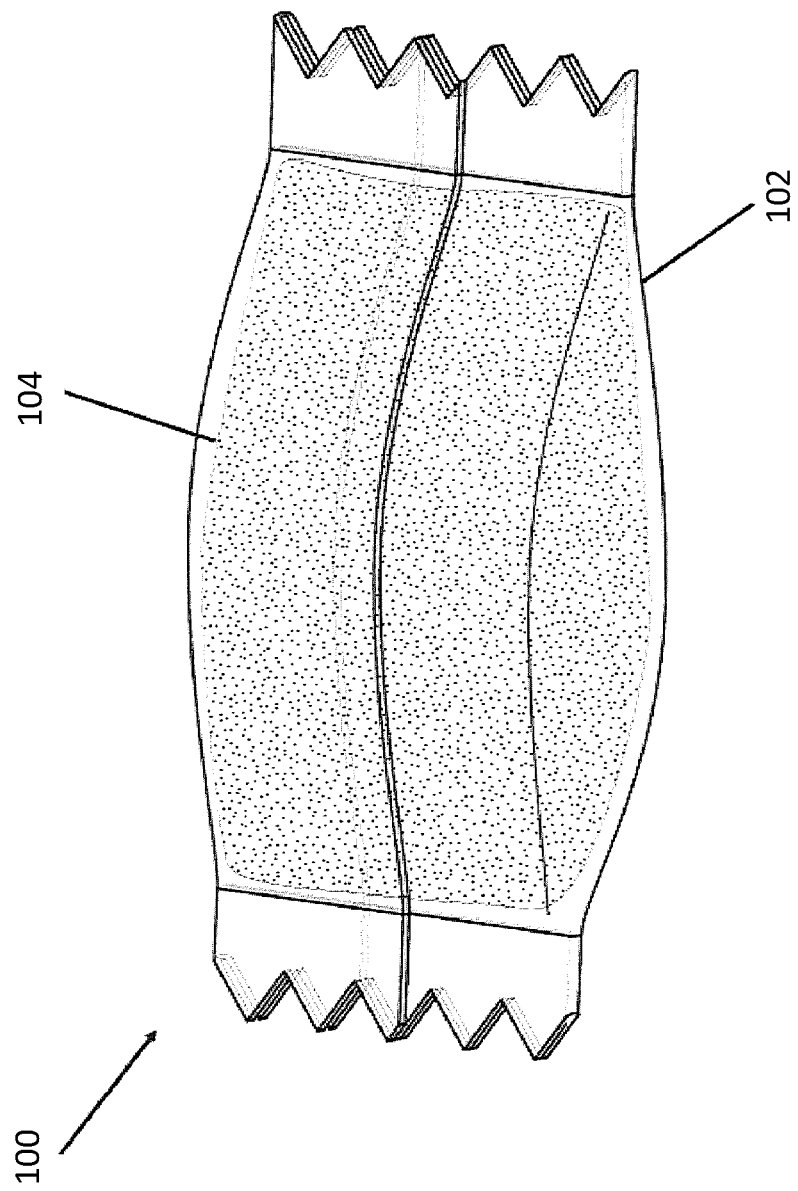

MOIST ORAL PRODUCT COMPRISING AN ACTIVE INGREDIENT

FIELD OF THE DISCLOSURE

The present disclosure relates to compositions intended for human use. The compositions are configured for oral use and deliver substances such as flavors and/or active ingredients during use. Such products may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

All-white snus portions are growing in popularity, and offer a discrete and aesthetically pleasing alternative to traditional snus. Such modern "white" pouched products may include a bleached tobacco or may be tobacco-free.

BRIEF SUMMARY

The present disclosure generally provides product compositions configured for oral use, the product compositions comprising a filler, at least one active ingredient, a salt, and at least one sweetener. The product composition has a moisture content of at least about 40% by weight, based on the total weight of the composition.

Accordingly, in one aspect, the disclosure provides a composition comprising a filler in an amount of at least 20% by weight, based on the total weight of the composition; at least one active ingredient comprising one or more botanical materials, stimulants, amino acids, vitamins, antioxidants, cannabinoids, pharmaceutical agents, or a combination thereof; a salt; and at least one sweetener; wherein the composition has a moisture content of at least about 40% by weight, based on the total weight of the composition. In some embodiments, the filler is microcrystalline cellulose.

In some embodiments, the composition further comprises a cellulose derivative.

In some embodiments, the salt is sodium chloride, ammonium chloride, or a combination thereof.

In some embodiments, the composition further comprises a taste modifier. In some embodiments, the taste modifier modifies one or more of bitter, sweet, salty, or sour tastes. In some embodiments, the taste modifier is selected from the group consisting of gamma-aminobutryic acid (GABA), adenosine monophosphate (AMP), lactisole, a vanilloid receptor agonist, an analgesic or anesthetic herb, menthol, eucalyptus, mint, and cinnamon. In some embodiments, the taste modifier is capsaicin.

In some embodiments, the active ingredient is a botanical material. In some embodiments, the botanical material is Korean ginseng.

In some embodiments, the active ingredient is a stimulant. In some embodiments, the stimulant is caffeine, theanine, or a combination thereof.

In some embodiments, the composition further comprises a vitamin as an additional active ingredient. In some embodiments, the vitamin is B6, B12, or a combination thereof.

In some embodiments, the composition further comprises an amino acid as an additional active ingredient. In some embodiments, the amino acid is taurine.

In some embodiments, the active ingredient is bleached.

In some embodiments, the composition is substantially free of tobacco.

In some embodiments, the composition comprises a nicotine component.

In some embodiments, the composition is substantially free of nicotine.

In some embodiments, the composition is enclosed in a pouch to form a pouched product.

The disclosure includes, without limitations, the following embodiments.

Embodiment 1: A composition comprising: a filler in an amount of at least 20% by weight, based on the total weight of the composition; at least one active ingredient comprising one or more botanical materials, stimulants, amino acids, vitamins, antioxidants, cannabinoids, pharmaceutical agents, or a combination thereof; a salt; and at least one sweetener; wherein the composition has a moisture content of at least about 40% by weight, based on the total weight of the composition.

Embodiment 2: The composition of embodiment 1, wherein the filler is microcrystalline cellulose.

Embodiment 3: The composition of any one of embodiments 1 or 2, further comprising a cellulose derivative.

Embodiment 4: The composition of any one of embodiments 1 to 3, wherein the salt is sodium chloride, ammonium chloride, or a combination thereof.

Embodiment 5: The composition of any one of embodiments 1 to 4, further comprising a taste modifier.

Embodiment 6: The composition of any one of embodiments 1 to 5, wherein the taste modifier modifies one or more of bitter, sweet, salty, or sour tastes.

Embodiment 7: The composition of any one of embodiments 1 to 6, wherein the taste modifier is selected from the group consisting of gamma-aminobutryic acid (GABA), adenosine monophosphate (AMP), lactisole, a vanilloid receptor agonist, an analgesic or anesthetic herb, menthol, eucalyptus, mint, and cinnamon.

Embodiment 8: The composition of any one of embodiments 1 to 7, wherein the taste modifier is capsaicin.

Embodiment 9: The composition of any one of embodiments 1 to 8, wherein the active ingredient is a botanical material.

Embodiment 10: The composition of any one of embodiments 1 to 9, wherein the botanical material is Korean ginseng.

Embodiment 11: The composition of any one of embodiments 1 to 10, wherein the active ingredient is a stimulant.

Embodiment 12: The composition of any one of embodiments 1 to 11, wherein the stimulant is caffeine, theanine, or a combination thereof.

Embodiment 13: The composition of any one of embodiments 1 to 12, further comprising a vitamin as an additional active ingredient.

Embodiment 14: The composition of any one of embodiments 1 to 13, wherein the vitamin is B6, B12, or a combination thereof.

Embodiment 15: The composition of any one of embodiments 1 to 14, further comprising an amino acid as an additional active ingredient.

Embodiment 16: The composition of any one of embodiments 1 to 15, wherein the amino acid is taurine.

Embodiment 17: The composition of any one of embodiments 1 to 16, wherein the composition is substantially free of tobacco.

Embodiment 18: The composition of any one of embodiments 1 to 17, wherein the composition is substantially free of nicotine.

Embodiment 19: The composition of any one of embodiments 1 to 18, wherein the active ingredient is bleached.

Embodiment 20: The composition of any one of embodiments 1 to 19, further comprising a flavoring agent.

Embodiment 21: The composition of any one of embodiments 1 to 20, wherein the composition is enclosed in a pouch to form a pouched product.

Embodiment 22: The composition of any one of embodiments 1 to 21, comprising ashwagandha.

Embodiment 23: The composition of any one of embodiments 1 to 22, comprising baobab.

Embodiment 24: The composition of any one of embodiments 1 to 23, comprising cordyceps.

Embodiment 25: The composition of any one of embodiments 1 to 24, comprising damiana.

Embodiment 26: The composition of any one of embodiments 1 to 25, comprising guarana.

Embodiment 27: The composition of any one of embodiments 1 to 26, comprising guarana, honey, and ashwagandha.

Embodiment 28: The composition of any one of embodiments 1 to 27, comprising maca.

Embodiment 29: The composition of any one of embodiments 1 to 28, comprising caffeine.

Embodiment 30: The composition of any one of embodiments 1 to 29, comprising theacrine.

Embodiment 31: The composition of any one of embodiments 1 to 30, comprising caffeine and theanine.

Embodiment 32: The composition of any one of embodiments 1 to 31, comprising taurine, theanine, phenylalanine, tyrosine, tryptophan, or a combination thereof.

Embodiment 33: The composition of any one of embodiments 1 to 32, comprising taurine and caffeine.

Embodiment 34: The composition of any one of embodiments 1 to 33, comprising taurine, caffeine, and guarana.

Embodiment 35: The composition of any one of embodiments 1 to 34, comprising taurine, maca, and cordyceps.

Embodiment 36: The composition of any one of embodiments 1 to 35, comprising theanine and caffeine.

Embodiment 37: The composition of any one of embodiments 1 to 36, comprising vitamin B6, vitamin B12, vitamin E, vitamin C, or a combination thereof.

Embodiment 38: The composition of any one of embodiments 1 to 37, comprising vitamin B6, caffeine, and theanine.

Embodiment 39: The composition of any one of embodiments 1 to 38, comprising vitamin B6, vitamin B12, and taurine.

Embodiment 40: The composition of any one of embodiments 1 to 39, comprising vitamin B6, vitamin B12, ginseng, and theanine.

Embodiment 41: The composition of any one of embodiments 1 to 40, comprising vitamin C, baobab, and chlorophyll.

Embodiment 42: The composition of any one of embodiments 1 to 41, comprising nicotine and ginseng.

Embodiment 43: The composition of any one of embodiments 1 to 42, comprising nicotine and caffeine.

Embodiment 44: The composition of any one of embodiments 1 to 43, comprising nicotine and guarana.

Embodiment 45: The composition of any one of embodiments 1 to 44, comprising cannabidiol (CBD).

Embodiment 46: The composition of any one of embodiments 1 to 45, comprising CBD, cocoa, and damiana.

Embodiment 47: The composition of any one of embodiments 1 to 46, comprising an active ingredient having a bitter taste, and a taste modifier which masks or blocks the perception of the bitter taste.

Embodiment 48: The composition of any one of embodiments 1 to 47, comprising caffeine and gamma-aminobutyric acid (GABA).

Embodiment 49: The composition of any one of embodiments 1 to 48, wherein the total amount of active ingredients is from 0.001% to about 20%.

Embodiment 50: A composition comprising: microcrystalline cellulose in an amount of from about 20% to about 40% by weight, based on the total weight of the composition; at least one active ingredient comprising one or more botanical materials, stimulants, amino acids, vitamins, or a combination thereof; sodium chloride; xylitol; sucralose; hydroxypropylcellulose, sodium alginate; sodium bicarbonate; propylene glycol; and a flavoring agent; wherein the composition has a moisture content of at least about 40% by weight, based on the total weight of the composition.

Embodiment 51: A composition configured to deliver an active ingredient to a user through contact with moisture in the mouth of the user, the composition comprising: a filler in an amount of at least 20% by weight, based on the total weight of the composition; at least one active ingredient comprising one or more botanical materials, stimulants, amino acids, vitamins, antioxidants, cannabinoids, pharmaceutical agents, or a combination thereof; a salt; and at least one sweetener; wherein the product composition has a moisture content of at least about 40% by weight, based on the total weight of the composition.

Embodiment 52: The composition of any one of embodiments 1 to 51, further comprising a nicotine component.

Embodiment 53: A method for modifying the flavor profile of an active ingredient in a composition, the composition comprising a filler in an amount of at least 20% by weight, based on the total weight of the composition; at least one active ingredient comprising one or more botanical materials, stimulants, amino acids, vitamins, antioxidants, cannabinoids, pharmaceutical agents, or a combination thereof; a salt; and at least one sweetener; wherein the product composition has a moisture content of at least about 40% by weight, based on the total weight of the composition; the method comprising providing a taste modifier in the product composition in an amount effective to mask or modify a taste sensation in the mouth of the user of the composition.

Embodiment 54: The method of embodiment 53, wherein the taste modifier is selected from the group consisting of an analgesic or anesthetic herb, spice, or flavor which produces a perceived cooling or warming effect, gamma-aminobutyric acid, capsaicin, and adenosine monophosphate.

Embodiment 55: The method of any one of embodiments 53 to 54, wherein the taste sensation is bitterness, sweetness, saltiness, or sourness.

Embodiment 56: The method of any one of embodiments 53 to 55, wherein the taste sensation is bitterness.

Embodiment 57: The method of any one of embodiments 53 to 56, wherein the taste modifier is capsaicin.

Embodiment 58: A method of preparing a composition comprising a filler in an amount of at least 20% by weight, based on the total weight of the composition; at least one active ingredient comprising one or more botanical materials, stimulants, amino acids, vitamins, antioxidants, cannabinoids, pharmaceutical agents, or a combination thereof; a salt; and at least one sweetener; wherein the product composition has a moisture content of at least about 40% by weight, based on the total weight of the composition; the method comprising mixing a filler, at least one active ingredient, and a salt to form a first mixture; and adding water to the first mixture to form the composition.

Embodiment 59: The method of any one of embodiments 53 to 58, wherein the composition further comprises a nicotine component.

Embodiment 60: The method of any one of embodiments 53 to 59, further comprising adding one or more binders to the first mixture. The method of the preceding embodiment, further comprising adding a buffer, one or more sweeteners, a humectant, a flavoring, or a combination thereof, to the first mixture.

Embodiment 61: The method of any one of embodiments 53 to 60, further comprising adding additional water to the composition.

Embodiment 62: The method of any one of embodiments 53 to 61, further comprising enclosing the composition in a pouch to form a pouched product.

Embodiment 63: The method of any one of embodiments 53 to 62, further comprising adding additional water to the pouched product.

Embodiment 64: A composition prepared by the method of any one of embodiments 53 to 63.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

Having thus described aspects of the disclosure in the foregoing general terms, reference will now be made to the accompanying drawings, which are not necessarily drawn to scale. The drawings are exemplary only, and should not be construed as limiting the disclosure.

FIG. 1 is a perspective view of a pouched product embodiment, taken across the width of the product, showing an outer pouch filled with a composition of the present disclosure.

DETAILED DESCRIPTION

The present disclosure provides products configured for oral use, the products including a filler in an amount of at least 20% by weight, based on the total weight of the composition, and an active ingredient including one or more botanical materials, stimulants, amino acids, vitamins, antioxidants, nicotine components, cannabinoids, pharmaceutical agents, or a combination thereof. The product composition further includes a salt and at least one sweetener. The product composition has a moisture content of at least about 40% by weight, based on the total weight of the composition.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the composition including water. Unless otherwise indicated, reference to "weight percent" of a composition reflects the total wet weight of the composition (i.e., including water).

The products as described herein comprise a filler, an active ingredient, a salt and at least one sweetener. The relative amounts of the various components within the composition may vary, and typically are selected so as to provide the desired sensory and performance characteristics to the oral product. The example individual components of the composition are described herein below.

Filler

Compositions as described herein include at least one filler. Such fillers may fulfill multiple functions, such as enhancing certain organoleptic properties such as texture and mouthfeel, enhancing cohesiveness or compressibility of the product, and the like. Generally, the fillers are porous particulate materials and are cellulose-based. For example, suitable fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials. Additional examples of potential fillers include maltodextrin, dextrose, calcium carbonate, calcium phosphate, lactose, mannitol, xylitol, and sorbitol. Combinations of fillers can also be used.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the composition based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "modified" starches. Other starches are obtained and subsequently modified. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, enzyme treatment, acetylation, hydroxypropylation, and/or partial hydrolysis. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, and starch sodium octenyl succinate.

In some embodiments, the filler is a cellulose material or a cellulose derivative. One particularly suitable filler for use in the products described herein is microcrystalline cellulose ("mcc"). The mcc may be synthetic or semi-synthetic, or it may be obtained entirely from natural celluloses. The mcc may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof In one embodiment, the composition comprises mcc as the filler. The quantity of mcc present in the composition as described herein may vary according to the desired properties.

The amount of filler can vary, but is typically greater than about 20%, and up to about 75% of the composition by weight, based on the total weight of the composition. A typical range of filler (e.g., mcc) within the composition can be from about 20 to about 75% by total weight of the composition, for example, from about 20, about 25, or about 30, to about 35, about 40, about 45, or about 50% by weight (e.g., about 20 to about 50%, or about 25 to about 45% by weight). In certain embodiments, the amount of filler is at least about 20% by weight, such as at least about 25%, or at least about 30%, or at least about 35%, or at least about 40%, based on the total weight of the composition.

Active Ingredient

The composition as disclosed herein includes one or more active ingredients. As used herein, an "active ingredient" refers to one or more substances belonging to any of the following categories: API (active pharmaceutical substances), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods". These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, vitamins, antioxidants, nicotine components, pharmaceutical ingredients (e.g., nutraceutical and medicinal ingredients), and cannabinoids. Each of these categories is further described herein below. The particular choice of active ingredients will vary depending upon the desired flavor, texture, and desired characteristics of the particular product.

The particular percentages of active ingredients present will vary depending upon the desired characteristics of the particular product. Typically, an active ingredient or combination thereof is present in a total concentration of at least about 0.001% by weight of the composition, such as in a range from about 0.001% to about 20%. In some embodiments, the active ingredient or combination of active ingredients is present in a concentration from about 0.1% w/w to about 10% by weight, such as, e.g., from about from about 0.5% w/w to about 10%, from about 1% to about 10%, from about 1% to about 5% by weight, based on the total weight of the composition. In some embodiments, the active ingredient or combination of active ingredients is present in a concentration of from about 0.001%, about 0.01%, about 0.1%, or about 1%, up to about 20% by weight, such as, e.g., from about from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the composition. Further suitable ranges for specific active ingredients are provided herein below.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species).

When present, a botanical is typically at a concentration of from about 0.01% w/w to about 10% by weight, such as, e.g., from about from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the composition.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein. Non-limiting examples of botanicals or botanical-derived materials include hemp, eucalyptus, rooibos, fennel, citrus, cloves, lavender, peppermint, chamomile, basil, rosemary, ginger, turmeric, green tea, white mulberry, cannabis, cocoa, ashwagandha, baobab, chlorophyll, cordyceps, damiana, ginseng, guarana, and maca. In some embodiments, the composition comprises green tea, turmeric, and white mulberry.

Ashwagandha (*Withania somnifera*) is a plant in the Solanaceae (nightshade) family. As an herb, Ashwagandha has found use in the Indian Ayurvedic system of medicine, where it is also known as "Indian Winter cherry" or "Indian Ginseng." In some embodiments, the active ingredient comprises ashwagandha.

Baobab is the common name of a family of deciduous trees of the genus *Adansonia*. The fruit pulp and seeds of the Baobab are consumed, generally after drying, as a food or nutritional supplement. In some embodiments, the active ingredient comprises baobab.

Chlorophyll is any of several related green pigments found in the mesosomes of cyanobacteria, as well as in the chloroplasts of algae and plants. Chlorophyll has been used as a food additive (colorant) and a nutritional supplement. Chlorophyll may be provided either from native plant materials (e.g., botanicals) or in an extract or dried powder form. In some embodiments, the active ingredient comprises chlorophyll.

Cordyceps is a diverse genus of ascomycete (sac) fungi which are abundant in humid temperate and tropical forests. Members of the cordyceps family are used extensively in traditional Chinese medicine. In some embodiments, the active ingredient comprises cordyceps.

Damiana is a small, woody shrub of the family Passifloraceae. It is native to southern Texas, Central America, Mexico, South America, and the Caribbean. Damiana produces small, aromatic flowers, followed by fruits that taste similar to figs. The extract from damiana has been found to suppress aromatase activity, including the isolated compounds pinocembrin and acacetin. In some embodiments, the active ingredient comprises damiana.

Guarana is a climbing plant in the family Sapindaceae, native to the Amazon basin. The seeds from its fruit, which are about the size of a coffee bean, have a high concentration of caffeine and, consequently, stimulant activity. In some embodiments, the active ingredient comprises guarana. In some embodiments, the active ingredient comprises guarana, honey, and ashwagandha.

Ginseng is the root of plants of the genus *Panax*, which are characterized by the presence of unique steroid saponin phytochemicals (ginsenosides) and gintonin. Ginseng finds use as a dietary supplement in energy drinks or herbal teas, and in traditional medicine. Cultivated species include Korean ginseng (*P. ginseng*), South China ginseng (*P. notoginseng*), and American ginseng (*P. quinquefolius*). American ginseng and Korean ginseng vary in the type and quantity of various ginsenosides present. In some embodiments, the active ingredient comprises ginseng. In some embodiments, the ginseng is American ginseng or Korean ginseng. In specific embodiments, the active ingredient comprises Korean ginseng.

Maca is a plant that grows in central Peru in the high plateaus of the Andes Mountains. It is a relative of the radish, and has an odor similar to butterscotch. Maca has been used in traditional (e.g., Chinese) medicine. In some embodiments, the active ingredient comprises maca.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis.

When present, a stimulant or combination of stimulants (e.g., caffeine, theacrine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

In some embodiments, the active ingredient comprises caffeine. In some embodiments, the active ingredient comprises theacrine. In some embodiments, the active ingredient comprises a combination of caffeine and thea.ctine.

Amino Acids

In some embodiments, the active ingredient comprises an amino acid. As used herein, the term "amino acid" refers to an organic compound that contains amine ($-NH_2$) and carboxyl ($-COOH$) or sulfonic acid ($SO_3H$) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-tranlational modification). Non-limiting examples of non-proteinogenic amino acids include gamma-aminobutyric acid (GABA), taurine (2-aminoethanesulfonic acid), theanine (L-γ-glutamylethlylamide), hydroxyproline, and beta-alanine.

When present, an amino acid or combination of amino acids (e.g., taurine, theanine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

In some embodiments, the amino acid is taurine, theanine, phenylalanine, tyrosine, tryptophan, or a combination thereof In some embodiments, the amino acid is taurine. In some embodiments, the active ingredient comprises a combination of taurine and caffeine. In some embodiments, the active ingredient comprises a combination of taurine, caffeine, and guarana. In some embodiments, the active ingredient comprises a combination of taurine, maca, and cordyceps. In some embodiments, the active ingredient comprises a combination of theanine and caffeine.

Vitamins

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones).

When present, a vitamin or combination of vitamins (e.g., vitamin B6, vitamin B12, vitamin E, vitamin C, or a combination thereof) is typically at a concentration of from about 0.01% w/w to about 1% by weight, such as, e.g., from about from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, or about 1% by weight, based on the total weight of the composition.

In some embodiments, the vitamin is vitamin B6, vitamin B12, vitamin E, vitamin C, or a combination thereof. In some embodiments, the active ingredient comprises a combination of vitamin B6, caffeine, and theanine. In some embodiments, the active ingredient comprises vitamin B6, vitamin B12, and taurine. In some embodiments, the active ingredient comprises a combination of vitamin B6, vitamin B12, ginseng, and theanine. In some embodiments, the active ingredient comprises a combination of vitamin C, baobab, and chlorophyll.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, bacopa monniera, withania somnifera, Lion's mane, and silybum marianum. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof In some embodiments, the antioxidant is Vitamin E or a derivative thereof, a flavonoid, a polyphenol, a carotenoid, or a combination thereof.

When present, an antioxidant is typically at a concentration of from about 0.001% w/w to about 10% by weight, such as, e.g., from about from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the composition.

Nicotine Component

In certain embodiments, the active ingredient comprises a nicotine component. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, the nicotine component is nicotine in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine component can be employed in the form of a salt. Salts of nicotine can be provided using the types of ingredients and techniques set forth in U.S. Pat. No. 2,033,909 to Cox et al. and Perfetti, Beitrage Tabakforschung Int., 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base) when present, is in a concentration of at least about 0.001% by weight of the composition, such as in a range from about 0.001% to about 10%. In some embodiments, the nicotine component is present in a concentration from about 0.1% w/w to about 10% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about from about 0.1% w/w to about 2.5%, from about 0.1% to about 2.0%, from about 0.1% to about 1.5%, or from about 0.1% to about 1% by weight, calculated as the free base and based on the total weight of the composition.

In some embodiments, the products or compositions of the disclosure can be characterized as completely free or substantially free of any nicotine component (e.g., any embodiment as disclosed herein may be completely or substantially free of any nicotine component). By "substantially free" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

In some embodiments, the active ingredient comprises a nicotine component (e.g., any product or composition of the disclosure, in addition to comprising any active ingredient or combination of active ingredients as disclosed herein, may further comprise a nicotine component). In some embodiments, the active ingredient comprises a combination of nicotine and ginseng. In some embodiments, the active ingredient comprises a combination of nicotine and caffeine. In some embodiments, the active ingredient comprises a combination of nicotine and guarana.

Cannabinoids

In some embodiments, the active ingredient comprises one or more cannabinoids. As used herein, the term "cannabinoid" refers to a class of diverse chemical compounds that acts on cannabinoid receptors, also known as the endocannabinoid system, in cells that alter neurotransmitter release in the brain. Ligands for these receptor proteins include the endocannabinoids produced naturally in the body by animals; phytocannabinoids, found in cannabis; and synthetic cannabinoids, manufactured artificially. Non-limiting examples of cannabinoids include tetrahydrocannabinol (THC), the primary psychoactive compound in cannabis, and cannabidiol (CBD) another major constituent of the plant, but which is devoid of psychoactivity. In some embodiments, the active ingredient comprises CBD. In some embodiments, the active ingredient comprises a combination of CBD, cocoa, and damiana.

When present, a cannabinoid (e.g., CBD) is typically in a concentration of at least about 0.1% by weight of the composition, such as in a range from about 0.1% to about 30%, such as, e.g., from about from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the composition.

Pharmaceutical Ingredients

The pharmaceutical ingredient can be any known agent adapted for therapeutic, prophylactic, or diagnostic use. These can include, for example, synthetic organic compounds, proteins and peptides, polysaccharides and other sugars, lipids, inorganic compounds, and nucleic acid sequences, having therapeutic, prophylactic, or diagnostic activity. Non-limiting examples of pharmaceutical ingredients include analgesics and antipyretics (e.g., acetylsalicylic acid, acetaminophen, 3-(4-isobutylphenyl)propanoic acid).

Bleached Active Ingredient

In some embodiments, the oral product comprises an active ingredient as disclosed herein, wherein the active ingredient is characterized as bleached. Such a bleached active ingredient may be desirable e.g., to prevent tooth discoloration during use of the oral product, or so that any residue remaining in the mouth of the user after use of the product is less visible, and is less likely to cause staining of fibrous materials, such as clothing, that may contact the residue. By "bleached" active ingredient is meant an active ingredient (e.g., a botanical material or derivative thereof), which, in its natural state possesses a color, and which has been treated to reduce or eliminate the color. By "color" is meant the characteristic of human visual perception described through color categories, with names such as red, blue, yellow (primary colors) or brown, orange, green, purple, and the like, resulting from combinations of primary colors. This perception of color derives from the stimulation of cone cells in the human eye by electromagnetic radiation in the visible spectrum, associated with objects through the wavelength of the light that is reflected from them. This reflection is governed by the object's physical properties such as e.g., absorption and emission spectra across the electromagnetic spectrum.

Certain active ingredients, by virtue of naturally occurring chemical compounds therein which reflect light in the visible range of the electromagnetic spectrum, impart a color to the active ingredient (e.g., chlorophyll or pigment decomposition products in certain botanical materials, responsible for green color and brown colors, respectively). Such chemical compounds, or a portion thereof, which are responsible for the color of the active ingredient, may be chemically altered or removed by various treatments. In some embodiments, the treatment is effective to eliminate at least 70% of the chemicals present in the active ingredient having maximum transmission of wavelengths in the visible range of the electromagnetic spectrum, based on the weight of the naturally occurring compounds. For example, such treatment may be effective to remove 70%, 80%, 90%, 95%, 99%, or even 100% of the naturally occurring compounds responsible for the visible color of the active ingredient.

In some embodiments, the treatment for bleaching (i.e., altering or removing colored chemical compounds from the active ingredient) includes extraction, chemical bleaching, or a combination thereof. One particularly suitable extraction method is supercritical carbon dioxide ($CO_2$) extraction. Methods of chemical bleaching of e.g., botanical materials, including tobacco, are known, and include as non-limiting examples, treatment with hydrogen peroxide, ozone, or other oxidizing agents. For example, bleached active ingredients (e.g., a bleached botanical or tobacco material) may be produced by various whitening methods using various bleaching or oxidizing agents. Example oxidizing agents include peroxides (e.g., hydrogen peroxide), chlorite salts, chlorate salts, perchlorate salts, hypochlorite salts, ozone, ammonia, potassium permanganate, and combinations thereof. Oxidation catalysts can be used. Example oxidation catalysts are titanium dioxide, manganese dioxide, and combinations thereof.

Methods of bleaching known for bleaching tobacco may be applied to the present active ingredients. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. No. 9,420,825 to Beeson et al.; and U.S. Pat. No. 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference.

In some embodiments, the bleached active agent, or the composition or product comprising the bleached active agent, can have an ISO brightness of at least about 50%, at least about 60%, at least about 65%, at least about 70%, at least about 75%, or at least about 80%. In some embodiments, the bleached active agent or the composition or product comprising the bleached active agent, can have an ISO brightness in the range of about 50% to about 90%, about 55% to about 75%, or about 60% to about 70%. ISO brightness can be measured according to ISO 3688:1999 or ISO 2470-1:2016.

In some embodiments, the bleached active agent can be characterized as lightened in color (e.g., "whitened") in comparison to an untreated active agent. White colors are often defined with reference to the International Commission on Illumination's (CIE's) chromaticity diagram. The bleached active agent or the composition or product comprising the bleached active agent, can, in certain embodiments, be characterized as closer on the chromaticity diagram to pure white than an untreated active agent or composition or product comprising an untreated active agent.

Whiteness values of bleached active ingredients, compositions, and pouched products comprising such ingredients, may be determined according to the Commission Internationale de l'Eclairage (CIE) model, for example, with a hand-held color meter, relative to a control product (See "Precise Color Communication; Color Control from Perception to Instrumentation," Konica Minolta, 2007; http://konicaminolta.com/instruments/about/network, which is incorporated herein by reference). Discoloration from white may be evaluated by the E313 Whiteness Index according to ASTM method E313, using the formula $WI=(3.388Z-3Y$, where Y and Z are the CIE tri-stimulus values, and measured by a hand-held meter.

Water

The moisture content (e.g., water content) of the composition, prior to use by a consumer of the product, may vary according to the desired properties. Typically, the composition, as present within e.g., a pouched product, prior to insertion into the mouth of the user, is less than about 60% by weight of water, and generally is from about 1 to about 60% by weight of water, for example, from about 5 to about 55%, about 10 to about 50%, about 20 to about 45%, or about 25 to about 40% water by weight, including water amounts of at least about 5% by weight, at least about 10% by weight, at least about 15% by weight, and at least about 20% by weight.

Taste Modifiers

In order to improve the organoleptic properties of a composition as disclosed herein, the composition may include one or more taste modifying agents ("taste modifiers") which may serve to mask, alter, block, or improve e.g., the flavor of a composition as described herein. Non-limiting examples of such taste modifiers include analgesic or anesthetic herbs, spices, and flavors which produce a perceived cooling (e.g., menthol, eucalyptus, mint), warming (e.g., cinnamon), or painful (e.g., capsaicin) sensation. Certain taste modifiers fall into more than one overlapping category.

In some embodiments, the taste modifier modifies one or more of bitter, sweet, salty, or sour tastes. In some embodiments, the taste modifier targets pain receptors. In some embodiments, the composition comprises an active ingredient having a bitter taste, and a taste modifier which masks or blocks the perception of the bitter taste. In some embodiments, the taste modifier is a substance which targets pain receptors (e.g., vanilloid receptors) in the user's mouth to mask e.g., a bitter taste of another component (e.g., an active ingredient). In some embodiments, the taste modifier is capsaicin.

In some embodiments, the taste modifier is the amino acid gamma-amino butyric acid (GABA), referenced herein above with respect to amino acids. Studies in mice suggest that GABA may serve function(s) in taste buds in addition to synaptic inhibition. See, e.g., Dvoryanchikov et al., J Neurosci. 2011 Apr. 13; 31(15): 5782-91. Without wishing to be bound by theory, GABA may suppress the perception of certain tastes, such as bitterness. In some embodiments, the composition comprises caffeine and GABA.

In some embodiments, the taste modifier is adenosine monophosphate (AMP). AMP is a naturally occurring nucleotide substance which can block bitter food flavors or enhance sweetness. It does not directly alter the bitter flavor, but may alter human perception of "bitter" by blocking the associated receptor.

In some embodiments, the taste modifier is lactisole. Lactisole is an antagonist of sweet taste receptors. Temporarily blocking sweetness receptors may accentuate e.g., savory notes.

When present, a representative amount of taste modifier is about 0.01% by weight or more, about 0.1% by weight or more, or about 1.0% by weight or more, but will typically make up less than about 10% by weight of the total weight of the composition, (e.g., from about 0.01%, about 0.05%, about 0.1%, or about 0.5%, to about 1%, about 5%, or about 10% by weight of the total weight of the composition).

In a still further aspect is provided a method for modifying the flavor profile of an active ingredient in a composition, the composition comprising a filler in an amount of at least 20%, based on the total weight of the composition; at least one active ingredient comprising one or more botanical materials, stimulants, amino acids, vitamins, antioxidants, nicotine components, cannabinoids, pharmaceutical agents, or a combination thereof; a salt; and at least one sweetener; wherein the product composition has a moisture content of at least about 40% by weight, based on the total weight of the composition; wherein the method comprises providing a taste modifier in the product composition in an amount effective to mask or modify a taste sensation in the mouth of the user of the composition. In some embodiments, the taste modifier selected from the group consisting of an analgesic or anesthetic herb, spice, or flavor which produces a perceived cooling or warming effect, gamma-aminobutyric acid, capsaicin, and adenosine monophosphate. In some embodiments, the taste sensation is bitterness, sweetness, saltiness, or sourness. In some embodiments, the taste sensation is bitterness. In some embodiments, the taste modifier is capsaicin.

Salts

In some embodiments, the composition comprises a salt (e.g., an alkali metal salt), typically employed in an amount sufficient to provide desired sensory attributes to the composition. Non-limiting examples of suitable salts include sodium chloride, potassium chloride, ammonium chloride, flour salt, sodium acetate, sodium citrate, and the like. In some embodiments, the salt is sodium chloride, ammonium chloride, or a combination thereof.

When present, a representative amount of salt is about 0.5% by weight or more, about 1.0% by weight or more, or about 1.5% by weight or more, but will typically make up about 10% or less of the total weight of the composition, or about 7.5% or less, or about 5% or less (e.g., from about 0.5 to about 5% by weight).

Sweeteners

In order to improve the sensory properties of the composition according to the disclosure, one or more sweeteners may be added. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, stevia, honey, and the like. Examples of artificial sweeteners include sucralose, isomaltulose, maltodextrin, saccharin, aspartame, acesulfame K, neotame, and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). In some embodiments, the sweetener is xylitol, sucralose, or a combination thereof.

When present, a sweetener or combination of sweeteners may make up from about 0.1 to about 20% or more of the of the composition by weight, for example, from about 0.1 to about 1%, from about 1 to about 5%, from about 5 to about 10%, or from about 10 to about 20% by weight, based on the total weight of the composition. In some embodiments, a combination of sweeteners is present at a concentration of from about 1% to about 3% by weight of the composition.

Flavoring Agents

In some embodiments, the composition comprises a flavoring agent. As used herein, a "flavoring agent" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. Specific types of flavors include, but are not limited to, vanilla, coffee, chocolate/cocoa, cream, mint, spearmint, menthol, peppermint, wintergreen, eucalyptus, lavender, cardamon, nutmeg, cinnamon, clove, cascarilla, sandalwood, honey, jasmine, ginger, anise, sage, licorice, lemon, orange, apple, peach, lime, cherry, strawberry, trigeminal sensates, terpenes and any combinations thereof. See also, Leffingwell et al., Tobacco Flavoring for Smoking Products, R. J. Reynolds Tobacco Company (1972), which is incorporated herein by reference. flavoring agents also may include components that are considered moistening, cooling or smoothening agents, such as eucalyptus. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The amount of flavoring agent utilized in the composition can vary, but is typically up to about 10% by weight, and certain embodiments are characterized by a flavoring agent content of at least about 0.1% by weight, such as about 0.5 to about 10%, about 1 to about 5%, or about 2 to about 4% weight, based on the total weight of the composition.

Binders

A binder (or combination of binders) may be employed in certain embodiments, in amounts sufficient to provide the desired physical attributes and physical integrity to the composition. Typical binders can be organic or inorganic, or a combination thereof. Representative binders include cellulose derivatives, povidone, sodium alginate, starch-based binders, pectin, carrageenan, pullulan, zein, and the like, and combinations thereof. A binder may be employed in amounts sufficient to provide the desired physical attributes and physical integrity to the composition. The amount of binder utilized in the composition can vary based on the binder and the desired composition properties, but is typically up to about 30% by weight, and certain embodiments are characterized by a binder content of at least about 0.1% by weight, such as about 0.5 to about 30% by weight, or about 1 to about 10% by weight, based on the total weight of the composition.

In one embodiment, the binder comprises a cellulose derivative. In certain embodiments, the cellulose derivative is a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose ("HPC"), hydroxypropylmethylcellulose ("HPMC"), hydroxyethyl cellulose, and carboxymethylcellulose ("CMC"). In one embodiment, the cellulose derivative is one or more of methylcellulose, HPC, HPMC, hydroxyethyl cellulose, and CMC. In some embodiments, the cellulose derivative is HPC. In one embodiment, the cellulose derivative is a combination of HPC and HPMC. In some embodiments, the composition comprises from about 1 to about 5% by weight of HPC, for example, from about 1%, about 2%, or about 3%, to about 4%, or about 5% by weight of the composition.

In certain embodiments, the binder includes a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the composition.

In certain embodiments, the binder includes an alginate (e.g., sodium or ammonium alginate). In certain embodiments, the binder comprises HPC and sodium alginate. When present, alginate binder materials are typically present in an amount of up to about 1% by weight, for example, from about 0.1, about 0.2, about 0.3, about 0.4, or about 0.5, to about 0.6, about 0.7, about 0.8, about 0.9, or about 1%, by weight, based on the total weight of the composition.

Buffering Agents

In certain embodiments, the composition of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Non-limiting examples of suitable buffers include alkali metals acetates, glycinates, phosphates, glycerophosphates, citrates, carbonates, hydrogen carbonates, borates, or mixtures thereof In some embodiments, the buffer is sodium bicarbonate.

Where present, the buffering agent is typically present in an amount less than about 5% by weight, based on the weight of the composition, for example, from about 0.1% to about 5%, such as, e.g., from about 0.1% to about 1%, or from about 0.1% to about 0.5% by weight, based on the total weight of the composition.

Colorants

A colorant may be employed in amounts sufficient to provide the desired physical attributes to the composition. Examples of colorants include various dyes and pigments, such as caramel coloring and titanium dioxide. The amount of colorant utilized in the composition can vary, but when present is typically up to about 3% by weight, such as from about 0.1%, about 0.5%, or about 1%, to about 3% by weight, based on the total weight of the composition.

Humectants

In certain embodiments, one or more humectants may be employed in the composition. Examples of humectants include, but are not limited to, glycerin, propylene glycol, and the like. Where included, the humectant is typically provided in an amount sufficient to provide desired moisture attributes to the composition. Further, in some instances, the humectant may impart desirable flow characteristics to the composition for depositing in a mold. In some embodiments, the humectant is propylene glycol.

When present, a humectant will typically make up about 5% or less of the weight of the composition (e.g., from about 0.1 to about 5% by weight), for example, from about 0.1% to about 1% by weight, or about 1% to about 5% by weight, based on the total weight of the composition.

Tobacco Material

In some embodiments, the composition may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis subsp. Hersperis, N. pauciflora, N. petunioides, N. quadrivalvis, N. repanda, N. rotundifolia, N. solanifolia,* and *N. spegazzinii*. Various representative other types of plants from the *Nicotiana* species are set forth in Goodspeed, The Genus *Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in Tobacco Production, Chemistry and Technology, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within a composition as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment.

In some embodiments, the tobacco material comprises tobacco leaf (lamina). The composition disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the mixture most preferably includes tobacco lamina, or a tobacco lamina and stem mixture (of which at least a portion is smoke-treated). Portions of the tobaccos within the mixture may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the d mixture optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15% by weight, or less than about % by weight. Most preferably, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. Preferably, tobacco parts or pieces are comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15% by weight to less than about 5% by weight. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25% by weight, often less than about 20%, and frequently less than about 15% by weight.

For the preparation of oral products, it is typical for a harvested plant of the Nicotiana species to be subjected to a curing process. The tobacco materials incorporated within the mixture for inclusion within products as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and Galpao tobaccos), Indian air cured, Red Russian and Rustica tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Pub. Nos. 8,434,496, 8,944, 072, and 8,991,403 to Chen et al., which are all incorporated herein by reference. In certain embodiments, this type of treatment is useful where the original tobacco material is subjected to heat in the processes previously described.

In various embodiments, the tobacco material can be treated to extract a soluble component of the tobacco material therefrom. "Tobacco extract" as used herein refers to the isolated components of a tobacco material that are extracted from solid tobacco pulp by a solvent that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

In some embodiments, the type of tobacco material is selected such that it is initially visually lighter in color than other tobacco materials to some degree (e.g., whitened or bleached). Tobacco pulp can be whitened in certain embodiments according to any means known in the art, and as described above in reference to color-eliminated active ingredients.

Typical inclusion ranges for tobacco materials can vary depending on the nature and type of the tobacco material, and the intended effect on the final composition, with an example range of up to about 30% by weight (or up to about 20% by weight or up to about 10% by weight or up to about 5% by weight), based on total weight of the composition (e.g., about 0.1 to about 15% by weight). In some embodiments, the products of the disclosure can be characterized as completely free or substantially free of tobacco material (other than purified nicotine as an active ingredient). For example, certain embodiments can be characterized as having less than 1% by weight, or less than 0.5% by weight, or less than 0.1% by weight of tobacco material, or 0% by weight of tobacco material.

Oral Care Additives

In some embodiments, the composition comprises an oral care ingredient (or mixture of such ingredients). Oral care ingredients provide the ability to inhibit tooth decay or loss, inhibit gum disease, relieve mouth pain, whiten teeth, or otherwise inhibit tooth staining, elicit salivary stimulation, inhibit breath malodor, freshen breath, or the like. For example, effective amounts of ingredients such as thyme oil, eucalyptus oil and zinc (e.g., such as the ingredients of formulations commercially available as ZYTEX® from Discus Dental) can be incorporated into the composition. Other examples of ingredients that can be incorporated in desired effective amounts within the present composition can include those that are incorporated within the types of oral care compositions set forth in Takahashi et al., Oral Microbiology and Immunology, 19(1), 61-64 (2004); U.S. Pat. No. 6,083,527 to Thistle; and US Pat. Appl. Pub. Nos. 2006/0210488 to Jakubowski and 2006/02228308 to Cummins et al. Other exemplary ingredients of tobacco containing-formulation include those contained in formulations marketed as MALTISORB® by Roquette and DENTIZYME® by NatraRx. When present, a representative amount of oral care additive is at least about 1%, often at least about 3%, and frequently at least about 5% of the total dry weight of the composition. The amount of oral care additive within the composition will not typically exceed about 30%, often will not exceed about 25%, and frequently will not exceed about 20%, of the total dry weight of the composition.

Other Additives

Other additives can be included in the disclosed composition. For example, the composition can be processed, blended, formulated, combined, and/or mixed with other materials or ingredients. The additives can be artificial, or can be obtained or derived from herbal or biological sources. Examples of further types of additives include thickening or gelling agents (e.g., fish gelatin), emulsifiers, preservatives (e.g., potassium sorbate and the like), disintegration aids, or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. Typical inclusion ranges for such additional additives can vary depending on the nature and function of the additive and the intended effect on the final composition, with an example range of up to about 10% by weight, based on total weight of the composition (e.g., about 0.1 to about 5% by weight).

The aforementioned additives can be employed together (e.g., as additive formulations) or separately (e.g., individual additive components can be added at different stages involved in the preparation of the final composition). Furthermore, the aforementioned types of additives may be encapsulated as provided in the final product or composition. Exemplary encapsulated additives are described, for example, in WO2010/132444 to Atchley, which has been previously incorporated by reference herein.

Preparation of the Composition

The manner by which the various components of the composition (e.g., filler, water, active ingredient, and the like) are combined may vary. As such, the overall composition with e.g., powdered composition components may be relatively uniform in nature. The components noted above, which may be in liquid or dry solid form, can be admixed in a pretreatment step prior to mixture with any remaining components of the composition, or simply mixed together with all other liquid or dry ingredients. The various components of the composition may be contacted, combined, or mixed together using any mixing technique or equipment known in the art. Any mixing method that brings the composition ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. In some embodiments, the components forming the composition are prepared such that the mixture thereof may be used in a starch molding process for forming the composition. Manners and methods for formulating compositions will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

In some embodiments, any one or more component, and the overall oral product described herein, can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, the column of sieves may be placed on or in a mechanical agitator. The agitator causes the vibration of each of the sieves in the column. The mechanical agitator may be activated for a pre-determined period of time in order to ensure that all particles are collected in the correct sieve. In some embodiments, the column of sieves is agitated for a period of time from 0.5 minutes to 10 minutes, such as from 1 minute to 10 minutes, such as from 1 minute to 5 minutes, such as for approximately 3 minutes. Once the agitation of the sieves in the column is complete, the material collected on each sieve is weighed. The weight of each sample on each sieve may then be divided by the total weight in order to obtain a percentage of the mass retained on each sieve. As the skilled person will readily appreciate, the screen opening sizes or mesh sizes for each sieve in the column used for sieve analysis may be selected based on the granularity or known maximum/minimum particle sizes of the sample to be analysed. In some embodiments, a column of sieves may be used for sieve analysis, wherein the column comprises from 2 to 20 sieves, such as from 5 to 15 sieves. In some embodiments, a column of sieves may be used for sieve analysis, wherein the column comprises 10 sieves. In some embodiments, the largest screen opening or mesh sizes of the sieves used for sieve analysis may be 1000 µm, such as 500 µm, such as 400 µm, such as 300 µm.

In some embodiments, any material referenced herein (e.g., filler, tobacco material, and the overall oral product) characterized as being in particulate form may have at least 50% by weight of particles with a particle size as measured by sieve analysis of no greater than about 1000 µm, such as no greater than about 500 µm, such as no greater than about 400 µm, such as no greater than about 350 µm, such as no greater than about 300 µm. In some embodiments, at least 60% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 70% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 80% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 90% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 95% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 99% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, approximately 100% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm.

In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 0.01 µm to about 1000 µm, such as from about 0.05 µm to about 750 µm, such as from about 0.1 µm to about 500 µm, such as from about 0.25 µm to about 500 µm. In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 10 µm to about 400 µm, such as from about 50 µm to about 350 µm, such as from about 100 µm to about 350 µm, such as from about 200 µm to about 300 µm.

In one embodiment is provided a method of preparing a composition as disclosed herein, the method comprising mixing a filler, at least one active ingredient, and a salt to form a first mixture; and adding water the first mixture to form the composition. In some embodiments, the method further comprises adding one or more binders to the first mixture. In some embodiments, the method further comprises adding a buffer, one or more sweeteners, a humectant, a flavoring, or a combination thereof, to the first mixture. In some embodiments, the method further comprises adding additional water to the composition.

In another aspect is provided a composition prepared by the method as disclosed herein.

Configured for Oral Use

Provided herein is a product configured for oral use. The term "configured for oral use" as used herein means that the product is provided in a form such that during use, saliva in the mouth of the user causes one or more of the components of the composition (e.g., flavoring agents and/or active ingredients) to pass into the mouth of the user. In certain embodiments, the product is adapted to deliver components to a user through mucous membranes in the user's mouth, the user's digestive system, or both, and, in some instances, said component is an active ingredient (including, but not limited to, for example, a stimulant, vitamin, taste modifier, or combination thereof) that can be absorbed through the mucous membranes in the mouth or absorbed through the digestive tract when the product is used.

Products configured for oral use as described herein may take various forms, including gels, pastilles, gums, lozenges, powders, and pouches. Gels can be soft or hard. Certain products configured for oral use are in the form of pastilles. As used herein, the term "pastille" refers to a dissolvable oral product made by solidifying a liquid or gel composition so that the final product is a somewhat hardened solid gel. The rigidity of the gel is highly variable. Certain products of the disclosure are in the form of solids. Certain products can exhibit, for example, one or more of the following characteristics: crispy, granular, chewy, syrupy, pasty, fluffy, smooth, and/or creamy. In certain embodiments, the desired textural property can be selected from the group consisting of adhesiveness, cohesiveness, density, dryness, fracturability, graininess, gumminess, hardness, heaviness, moisture absorption, moisture release, mouthcoating, roughness, slipperiness, smoothness, viscosity, wetness, and combinations thereof.

The products comprising the compositions of the present disclosure may be dissolvable. As used herein, the terms "dissolve," "dissolving," and "dissolvable" refer to compositions having aqueous-soluble components that interact with moisture in the oral cavity and enter into solution, thereby causing gradual consumption of the product. According to one aspect, the dissolvable product is capable of lasting in the user's mouth for a given period of time until it completely dissolves. Dissolution rates can vary over a wide range, from about 1 minute or less to about 60 minutes. For example, fast release compositions typically dissolve and/or release the active substance in about 2 minutes or less, often about 1 minute or less (e.g., about 50 seconds or less, about 40 seconds or less, about 30 seconds or less, or about 20 seconds or less). Dissolution can occur by any means, such as melting, mechanical disruption (e.g., chewing), enzymatic or other chemical degradation, or by disruption of the interaction between the components of the composition. In some embodiments, the product can be meltable as discussed, for example, in US Patent App. Pub. No. 2012/0037175 to Cantrell et al. In other embodiments, the products do not dissolve during the product's residence in the user's mouth.

In one embodiment, the product comprising the composition of the present disclosure is in the form of a composition disposed within a moisture-permeable container (e.g., a water-permeable pouch). Such compositions in the water-permeable pouch format are typically used by placing one pouch containing the composition in the mouth of a human subject/user. Generally, the pouch is placed somewhere in the oral cavity of the user, for example under the lips, in the same way as moist snuff products are generally used. The pouch preferably is not chewed or swallowed. Exposure to saliva then causes some of the components of the composition therein (e.g., flavoring agents and/or active ingredients) to pass through e.g., the water-permeable pouch and provide the user with flavor and satisfaction, and the user is not required to spit out any portion of the composition. After about 10 minutes to about 60 minutes, typically about 15 minutes to about 45 minutes, of use/enjoyment, substantial amounts of the composition have been absorbed through oral mucosa of the human subject, and the pouch may be removed from the mouth of the human subject for disposal.

Accordingly, in certain embodiments, the composition as disclosed herein and any other components noted above are combined within a moisture-permeable packet or pouch that acts as a container for use of the composition to provide a pouched product configured for oral use. Certain embodiments of the disclosure will be described with reference to FIG. 1 of the accompanying drawings, and these described embodiments involve snus-type products having an outer pouch and containing a composition as described herein. As explained in greater detail below, such embodiments are provided by way of example only, and the pouched products of the present disclosure can include the composition in other forms. The composition/construction of such packets or pouches, such as the container pouch 102 in the embodiment illustrated in FIG. 1, may be varied. Referring to FIG. 1, there is shown a first embodiment of a pouched product 100. The pouched product 100 includes a moisture-permeable container in the form of a pouch 102, which contains a material 104 comprising a composition as described herein.

Suitable packets, pouches or containers of the type used for the manufacture of smokeless tobacco products are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. The composition may be contained in pouches and packaged, in a manner and using the types of components used for the manufacture of conventional snus types of products. The pouch provides a liquid-permeable container of a type that may be considered to be similar in character to the mesh-like type of material that is used for the construction of a tea bag. Components of the composition readily diffuse through the pouch and into the mouth of the user.

Non-limiting examples of suitable types of pouches are set forth in, for example, U.S. Pat. No. 5,167,244 to Kjerstad and U.S. Pat. No. 8,931,493 to Sebastian et al.; as well as US Patent App. Pub. Nos. 2016/0000140 to Sebastian et al.; 2016/0073689 to Sebastian et al.; 2016/0157515 to Chapman et al.; and 2016/0192703 to Sebastian et al., each of which is incorporated herein by reference. Pouches can be provided as individual pouches, or a plurality of pouches (e.g., 2, 4, 5, 10, 12, 15, 20, 25 or 30 pouches) can be connected or linked together (e.g., in an end-to-end manner) such that a single pouch or individual portion can be readily removed for use from a one-piece strand or matrix of pouches.

An example pouch may be manufactured from materials, and in such a manner, such that during use by the user, the pouch undergoes a controlled dispersion or dissolution. Such pouch materials may have the form of a mesh, screen, perforated paper, permeable fabric, or the like. For example, pouch material manufactured from a mesh-like form of rice paper, or perforated rice paper, may dissolve in the mouth of the user. As a result, the pouch and composition each may undergo complete dispersion within the mouth of the user during normal conditions of use, and hence the pouch and composition both may be ingested by the user. Other examples of pouch materials may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the composition contents permeate through the pouch material prior to the time that the pouch undergoes loss of its physical integrity. If desired, flavoring ingredients, disintegration aids, and other desired components, may be incorporated within, or applied to, the pouch material.

The amount of material contained within each product unit, for example, a pouch, may vary. In some embodiments, the weight of the composition within each pouch is at least about 50 mg, for example, from about 50 mg to about 1 gram, from about 100 to 800 about mg, or from about 200 to about 700 mg. In some smaller embodiments, the weight of the composition within each pouch may be from about 100 to about 300 mg. For a larger embodiment, the weight of the material within each pouch may be from about 300 mg to about 700 mg. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

In certain embodiments, one or more active ingredients as described herein are included in the composition within the pouched product, and one or more further active ingredients are disposed in or on the external surface of the product (e.g., on or in the pouch material as disclosed herein). In some embodiments, separate location of the active ingredients may allow differential release profiles (e.g., one active ingredient may be rapidly available to the mouth and/or digestive system, and the other active ingredient may be released more gradually with product use).

A pouched product as described herein can be packaged within any suitable inner packaging material and/or outer container. See also, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 8,397,945 to Gelardi et al., D592,956 to Thiellier; D594,154 to Patel et al.; and D625,178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; 2010/0264157 to Bailey et al.; and 2011/0168712 to Bailey et al. which are incorporated herein by reference.

In a further aspect is provided a composition configured to deliver an active ingredient to a user through contact with moisture in the mouth, the composition comprising a filler in an amount of at least 20% by weight, based on the total weight of the composition; at least one active ingredient comprising one or more botanical materials, stimulants, amino acids, vitamins, antioxidants, nicotine components, cannabinoids, pharmaceutical agents, or a combination thereof; a salt; and at least one sweetener; wherein the product composition has a moisture content of at least about 40% by weight, based on the total weight of the composition.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXAMPLES

Aspects of the present invention are more fully illustrated by the following examples, which are set forth to illustrate certain aspects of the present invention and are not to be construed as limiting thereof.

Example 1

Pouched Product with Caffeine and Theanine

Samples of pouched products according to embodiments of the present disclosure were prepared from a composition comprising caffeine and theanine as the active ingredients, and microcrystalline cellulose (mcc), water, and additional components as disclosed herein (salt, binder, cellulose derivative, sweeteners, humectant, buffer, and flavoring agent). The composition was prepared by combining microcrystalline cellulose (138.95 g, 28% of the composition by weight), hydroxypropyl cellulose (15 g, 3% of the composition by weight), caffeine (30.2 g, 6% of the composition by weight), theanine (26.95 g, 5.4% of the composition by weight), a salt (20 g, 4% of the composition by weight) and a binder (3.5 g, 0.7% of the composition by weight) to form a mixture of dry ingredients. To the mixture of dry ingredients was added water (59.5 g, 11.9% of the composition by weight), buffer (1.3 g, 0.26% of the composition by weight), sweeteners (10.3 g, 2.06% of the composition by weight), humectant (4.45 g, 0.89% of the composition by weight), and flavoring agent (5.85 g, 1.17% of the composition by weight). Portions of the composition (442.4 mg) were placed into pouches for a product weight of 476 mg and additional water (32% by weight) was sprayed onto the product for a final pouch weight of 700 mg. The moisture content of the pouched product was 48%, and the pH of the contents was 7.71.

Example 2

Pouched Product with Caffeine, Theanine, and Vitamin B6

Samples of pouched products according to embodiments of the present disclosure were prepared according to the procedure of Example 1, but adding vitamin B6 in an amount of 0.2 g (0.04% of the composition by weight). Portions of the composition (442.4 mg) were placed into pouches and additional water (32% by weight) was added for a final pouch weight of 700 mg. The moisture content of the pouched product was 48%, and the pH of the contents was 7.74.

Example 3

Pouched Product with Caffeine, Theanine, and Vitamin B6

Samples of pouched products according to embodiments of the present disclosure were prepared from a composition comprising caffeine, theanine, and vitamin B6 as the active ingredients, and microcrystalline cellulose (mcc), water, and additional components as disclosed herein (salt, binder, cellulose derivative, sweeteners, humectant, buffer, flavoring agent).

The composition was prepared by combining microcrystalline cellulose (273.75 g, 36.5% of the composition by weight), hydroxypropyl cellulose (22.5 g, 3% of the composition by weight), caffeine (45.3 g, 6% of the composition by weight), theanine (40.43 g, 5.4% of the composition by weight), a salt (30 g, 4% of the composition by weight) and a binder (5.25 g, 0.7% of the composition by weight) to form a mixture of dry ingredients. To the mixture of dry ingredients was added water (60 g, 8% of the composition by weight), buffer (1.95 g, 0.26% of the composition by weight), vitamin B6 (0.3 g of the hydrochloride salt, 0.04% of the composition by weight), sweeteners (15.1 g, 2.01% of the composition by weight), humectant (6.68 g, 0.89% of the composition by weight), and flavoring agent (8.78 g, 1.17% of the composition by weight). Portions of the composition (442.4 mg) were placed into pouches for a product weight of 476 mg, and additional water (32% by weight) was sprayed onto the product for a final pouch weight of 700 mg. The moisture content of the pouched product was 40%, and the pH of the contents was 7.85.

Example 4

Pouched Product with Caffeine and GABA

Samples of pouched products according to embodiments of the present disclosure were prepared from a composition comprising caffeine and gamma-aminobutyric acid (GABA) as the active ingredients, microcrystalline cellulose (mcc), water, and additional components as disclosed herein (salt, binder, cellulose derivative, sweeteners, humectant, buffer, flavoring agent). The composition was prepared by combining microcrystalline cellulose (355.8 g, 35.6% of the composition by weight), caffeine (60.4 g, 6% of the composition by weight), a salt (40 g, 4% of the composition by weight) and a binder (7 g, 0.7% of the composition by weight) to form a mixture of dry ingredients. To the mixture of dry ingredients was added water (119 g, 11.9% of the composition by weight), buffer (2.6 g, 0.26% of the composition by weight), GABA (6.04 g, 0.6% of the composition by weight), sweeteners (20.6 g, 2.06% of the composition by weight), humectant (8.9 g, 0.89% of the composition by weight), and flavoring agent (11.7 g, 1.17% of the composition by weight). Portions of the composition (442.4 mg) were placed into pouches for a product weight of 476 mg, and additional water (32% by weight) was sprayed onto the product for a final pouch weight of 700 mg. The moisture content of the pouched product was 48%, and the pH of the contents was 9.2.

Example 5

Pouched Product with Taurine

Samples of pouched products according to embodiments of the present disclosure were prepared from a composition comprising taurine as the active ingredient, microcrystalline cellulose (mcc), water, and additional components as disclosed herein (salt, binder, cellulose derivative, sweeteners, humectant, buffer, flavoring agent). The composition was prepared by combining microcrystalline cellulose (281.1 g, 28.1% of the composition by weight), hydroxypropyl cellulose (30 g, 3% of the composition by weight), taurine (107.8 g, 10.78% of the composition by weight), a salt (40 g, 4% of the composition by weight) and a binder (7 g, 0.7% of the composition by weight) to form a mixture of dry ingredients. To the mixture of dry ingredients was added water (119 g, 11.9% of the composition by weight), buffer (2.6 g, 0.26% of the composition by weight), sweeteners (20.6 g, 2.06% of the composition by weight), humectant (8.9 g, 0.89% of the composition by weight), and flavoring agent (1.5% of the composition by weight). Portions of the composition (442.4 mg) were placed into pouches for a product weight of 476 mg, and additional water (32% by weight) was sprayed onto the product for a final pouch weight of 700 mg. The moisture content of the pouched product was 48%, and the pH of the contents was 7.36.

Example 6

Pouched Product with Taurine and Caffeine

Samples of pouched products according to embodiments of the present disclosure were prepared from a composition comprising taurine and caffeine as the active ingredients, microcrystalline cellulose (mcc), water, and additional components as disclosed herein (salt, binder, cellulose derivative, sweeteners, humectant, buffer, flavoring agent). The composition was prepared by combining microcrystalline cellulose (365 g, 36.5% of the composition by weight), taurine (80 g, 8% of the composition by weight), caffeine (60.4 g, 6.04% of the composition by weight) a salt (40 g, 4% of the composition by weight) and a binder (7 g, 0.7% of the composition by weight) to form a mixture of dry ingredients. To the mixture of dry ingredients was added water (80 g, 8% of the composition by weight), buffer (2.6 g, 0.26% of the composition by weight), sweeteners (20.6 g, 2.06% of the composition by weight), humectant (8.9 g, 0.89% of the composition by weight), and flavoring agent (16 g, 1.6% of the composition by weight). Portions of the composition (442.4 mg) were placed into pouches for a product weight of 476 mg, and additional water (32% by weight) was sprayed onto the product for a final pouch weight of 700 mg. The moisture content of the pouched product was 40%.

Example 7

Pouched Product with Taurine, Guarana, and Caffeine

Samples of pouched products according to embodiments of the present disclosure were prepared according to the procedure of Example 6, but adding guarana (10 g, 1% of the composition by weight). Portions of the composition (442.4 mg) were placed into pouches for a product weight of 476 mg, and additional water (32% by weight) was sprayed onto the product for a final pouch weight of 700 mg. The moisture content of the pouched product was 40%.

Example 8

Pouched Product with American Ginseng

Samples of pouched products according to embodiments of the present disclosure were prepared from a composition comprising taurine and caffeine as the active ingredients, microcrystalline cellulose (mcc), water, and additional components as disclosed herein (salt, binder, cellulose derivative, sweeteners, humectant, buffer, flavoring agent). The composition was prepared by combining microcrystalline cellulose (320.55 g, 42.74% of the composition by weight), ginseng root powder (6.3 g, 0.84% of the composition by weight), a salt (17.25 g, 2.3% of the composition by weight) and a binder (5.25 g, 0.7% of the composition by weight) to form a mixture of dry ingredients. To the mixture of dry ingredients was added water (33.75 g, 4.5% of the composition by weight), buffer (1.95 g, 0.26% of the composition by weight), sweeteners (15.75 g, 2.06% of the composition by weight), humectant (4.5 g, 0.6% of the composition by weight), and flavoring agent (69 g, 9.2% of the composition by weight). Portions of the composition (442.4 mg) were placed into pouches for a product weight of 476 mg, and additional water (32% by weight) was sprayed onto the product for a final pouch weight of 700 mg. The moisture content of the pouched product was 48%.

Example 9

Pouched Product with Korean Ginseng

Samples of pouched products according to embodiments of the present disclosure were prepared according to the procedure of Example 8, but using Korean (Panax) ginseng. Portions of the composition (442.4 mg) were placed into pouches for a product weight of 476 mg, and additional water (32% by weight) was sprayed onto the product for a final pouch weight of 700 mg. The moisture content of the pouched product was 48%.

Example 10

Sensory Preference

Samples of embodiments of pouched products according to Examples 8 and 9 were evaluated by a six-person, internal expert sensory panel. Each sample was evaluated for subjective sensory preference. Both products were deemed acceptable, with the off notes expected from ginseng present and aligned with expectations. Example 8 was noted as astringent and earthy, with somewhat inconsistent flavor delivery. In contrast, Example 9 (Korean ginseng) delivered more complex and consistent flavor, and produced more mouth action, tingle, and warmth on the tongue. Overall, the panel's unanimous preference was for Example 9 over Example 8 (margin of 6 to 0). The sensory data demonstrated that Korean ginseng provided a composition with a superior sensory experience relative to a composition containing American ginseng.

What is claimed is:

1. A composition, comprising:
a filler in an amount of at least 20% by weight, based on the total weight of the composition;
at least one active ingredient comprising one or more botanical materials, stimulants, amino acids, vitamins, antioxidants, cannabinoids, pharmaceutical agents, or a combination thereof;
a salt; and
at least one sweetener;
wherein the composition is substantially free of nicotine.

2. The composition of claim 1, wherein the filler is microcrystalline cellulose.

3. The composition of claim 1, further comprising a cellulose derivative selected from the group consisting of methylcellulose, hydroxypropylcellulose, hydroxypropylmethylcellulose, hydroxyethyl cellulose, carboxymethylcellulose, and combinations thereof.

4. The composition of claim 1, wherein the salt is sodium chloride, ammonium chloride, or a combination thereof.

5. The composition of claim 1, further comprising a taste modifier.

6. The composition of claim 5, wherein the taste modifier modifies one or more of bitter, sweet, salty, or sour tastes.

7. The composition of claim 5, wherein the taste modifier is selected from the group consisting of gamma-aminobutyric acid (GABA), adenosine monophosphate (AMP), lactisole, a vanilloid receptor agonist, an analgesic or anesthetic herb, menthol, eucalyptus, mint, and cinnamon.

8. The composition of claim 5, wherein the taste modifier is capsaicin.

9. The composition of claim 1, wherein the active ingredient is a botanical material.

10. The composition of claim 9, wherein the botanical material is Korean ginseng.

11. The composition of claim 1, wherein the active ingredient is a stimulant selected from the group consisting of caffeine, theanine, and combinations thereof.

12. The composition of claim 11, further comprising a vitamin, an amino acid, or a combination thereof, as an additional active ingredient.

13. The composition of claim 12, wherein the vitamin is B6, B12, or a combination thereof.

14. The composition of claim 12, wherein the amino acid is taurine.

15. The composition of claim 1, wherein the composition is substantially free of tobacco.

16. The composition of claim 1, wherein the active ingredient is bleached.

17. The composition of claim 1, wherein the composition is enclosed in a pouch to form a pouched product.

18. The composition of claim 1, wherein the filler is microcrystalline cellulose, the composition further comprising hydroxypropyl cellulose in an amount by weight from about 1% to about 5%, based on the total weight of the composition.

19. The composition of claim 1, wherein the moisture content of the composition is from about 1% to about 60% by weight, based on the total weight of the composition.

20. The composition of claim 1, wherein the moisture content of the composition is from about 20% to about 45% by weight, based on the total weight of the composition.

21. The composition of claim 1, wherein the active ingredient comprises vitamin B3, vitamin B6, and caffeine.

22. The composition of claim 1, wherein the active ingredient comprises vitamin B3, vitamin B6, caffeine, and theanine.

23. The composition of claim 1, wherein the active ingredient comprises tryptophan and theanine.

24. The composition of claim 23, further comprising chamomile.

* * * * *